(12) United States Patent
Heirtzler et al.

(10) Patent No.: US 6,381,547 B1
(45) Date of Patent: Apr. 30, 2002

(54) TIRE DEFECT DETECTION SYSTEM AND METHOD

(75) Inventors: Frank J. Heirtzler, Londonderry, NH (US); Wayne S. Hill, Westborough, MA (US)

(73) Assignee: Foster-Miller, Inc., Waltham, MA (US)

( * ) Notice: Subject to any disclaimer, the term of this patent is extended or adjusted under 35 U.S.C. 154(b) by 66 days.

(21) Appl. No.: 09/591,726

(22) Filed: Jun. 12, 2000

(51) Int. Cl.⁷ .............................. G06F 19/00; G01M 1/00
(52) U.S. Cl. .............................. 702/39; 702/35; 702/39; 702/56; 73/146; 73/462
(58) Field of Search .............................. 702/35, 39, 56, 702/76–77, 105–106; 73/146, 462, 618, 658–660

(56) References Cited

U.S. PATENT DOCUMENTS

| | | | |
|---|---|---|---|
| 4,936,138 A | * | 6/1990 | Cushman et al. .............. 73/146 |
| 5,095,744 A | * | 3/1992 | Macecek et al. .............. 73/146 |
| 5,614,676 A | * | 3/1997 | Dutt et al. .............. 702/77 |
| 5,845,232 A | * | 12/1998 | Shively et al. .............. 702/105 |

* cited by examiner

*Primary Examiner*—Bryan Bui
(74) *Attorney, Agent, or Firm*—Iandiorio & Teska

(57) ABSTRACT

A tire defect detection system including a support structure for receiving a tire; an actuator disposed proximate the tire for impacting the tire; a microphone disposed proximate the actuator for receiving a sound wave generated when the actuator impacts the tire; and a computer responsive to the microphone, the computer programmed to calculate a number of discriminator quantities from the resulting sound wave and to compare the calculated discriminator quantities with stored discriminator quantities indicative of a defect to determine whether a defect is present in the tire.

33 Claims, 33 Drawing Sheets

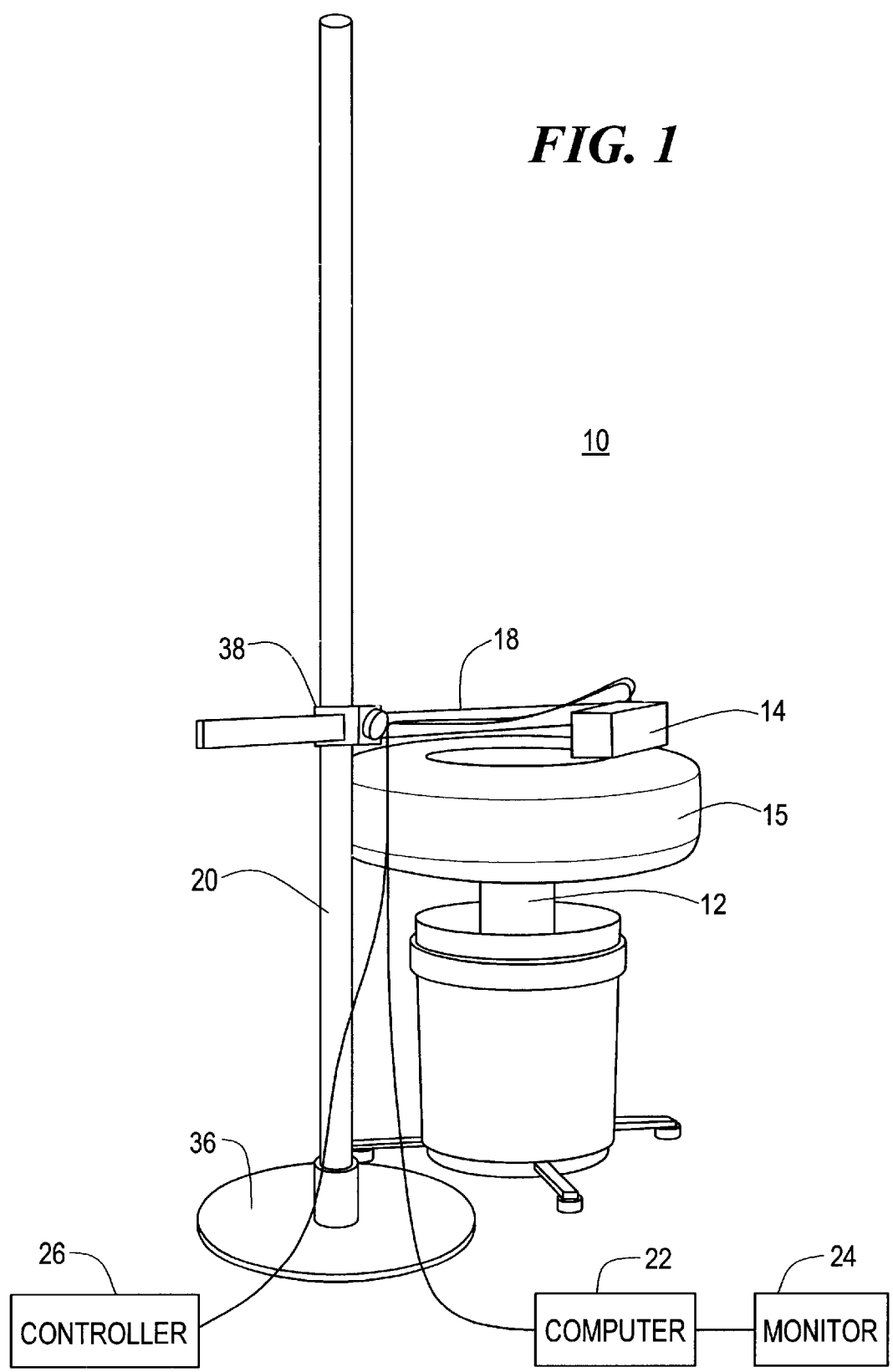

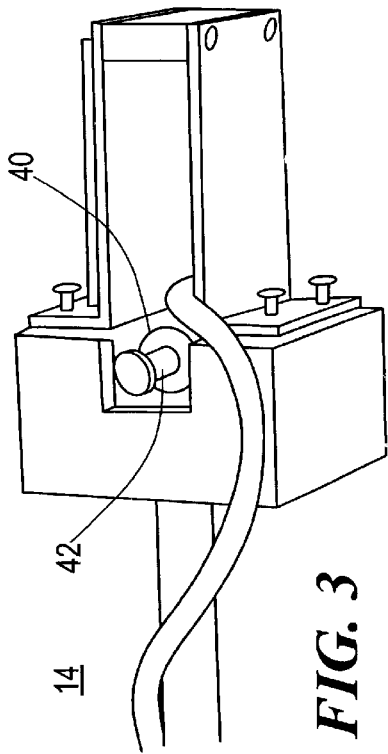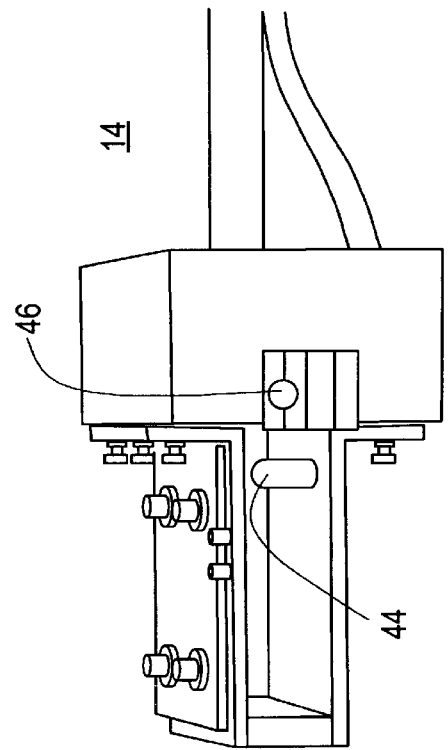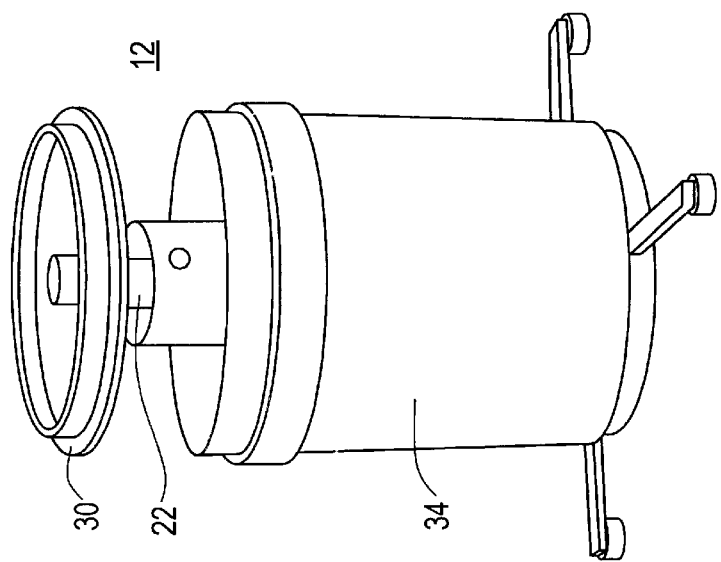

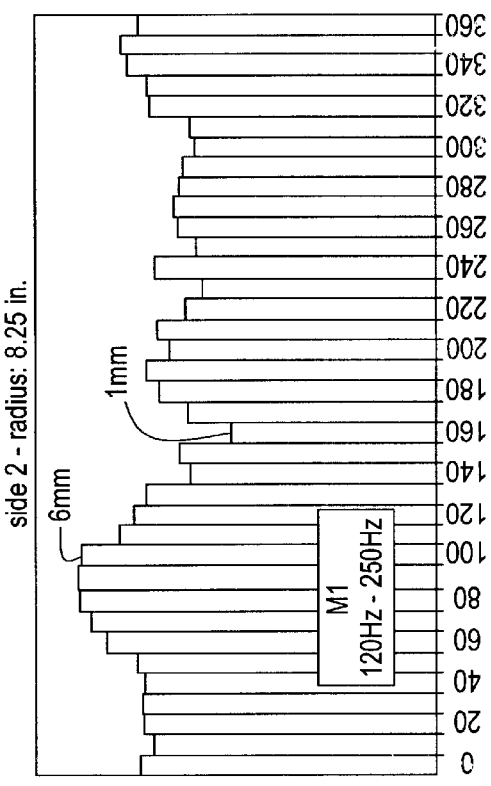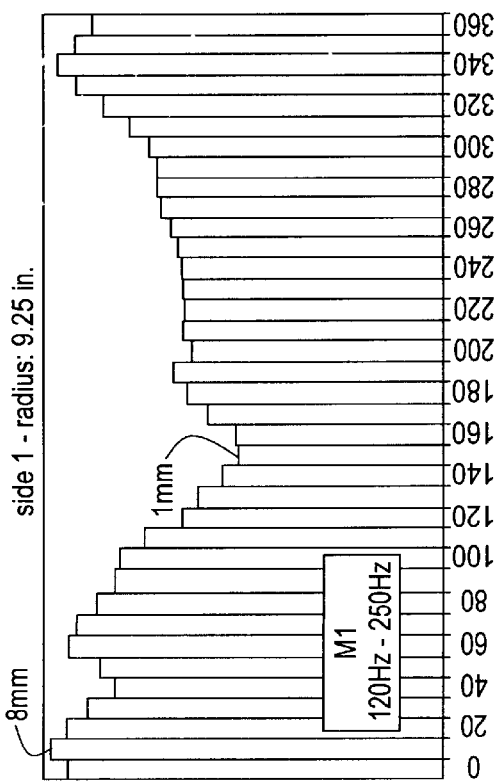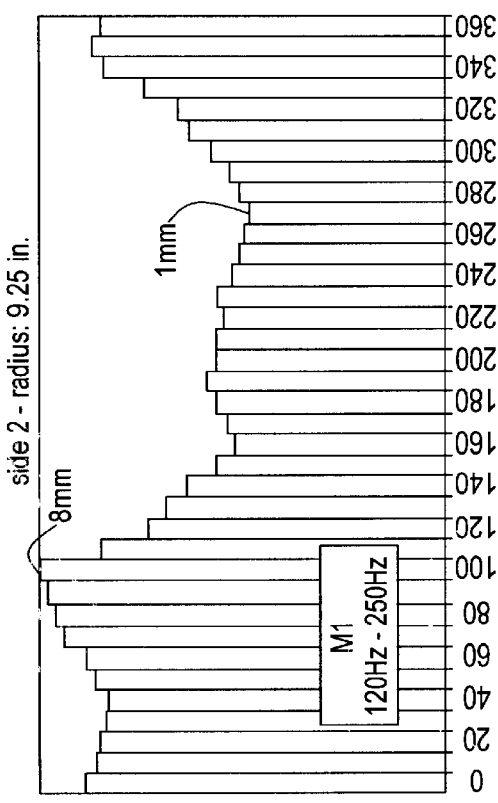

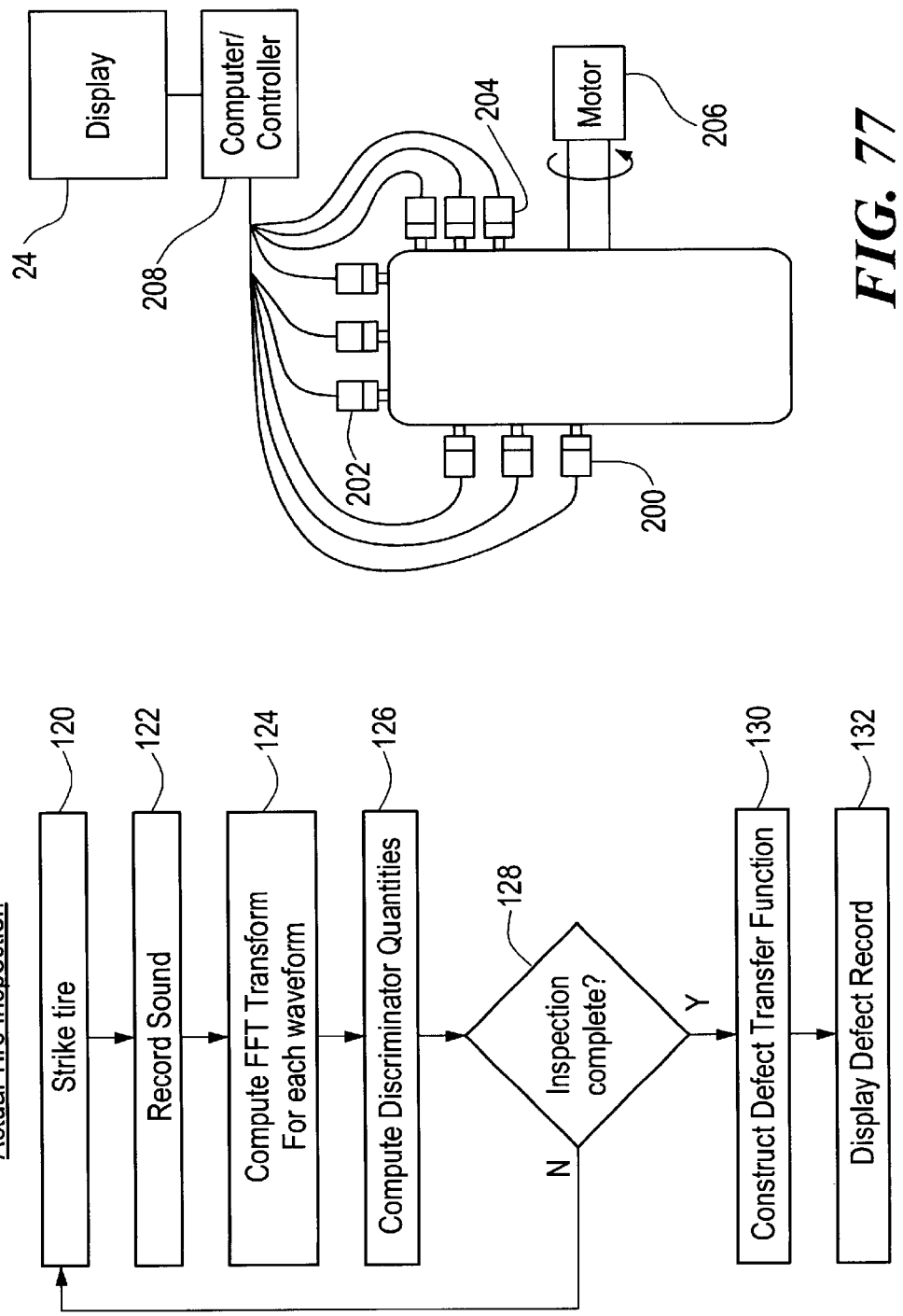

TIRE DEFECT DETECTION SYSTEM AND METHOD

GOVERNMENT RIGHTS NOTICE

This invention was developed with finds under Contract No: N68335-97-C-0201. The United States Government may have certain rights in this invention.

FIELD OF INVENTION

This invention relates to a system and method for detecting and locating defects such as delaminations and cuts in various types of tires.

BACKGROUND OF INVENTION

Over twenty five million retreaded tires were sold in the United States in 1995 alone. Retreaded tires are used in critical applications such as for military and commercial aircraft and even school buses. As such, when a retreaded tire fails due to a delamination, the result can be disastrous.

There have been numerous attempts made to devise inspection devices which can detect defects present in a tire after the tire has been retreaded. Such prior art devices, however, suffer from numerous drawbacks. Holography methods, which map tire defects using optical means are extremely expensive, generally about $500,000 per machine, are extremely sensitive to vibration, and also relatively slow. Shearography is a similar technique less sensitive to vibration, but also very expensive and slow. High voltage tests are less expensive, but are limited to detecting only metal inclusions in the tire carcass. Ultrasound techniques are capable only of detecting air-filled defects, are very sensitive to the thickness of the tire wall being measured, and therefore are not generally used to inspect aircraft tires. The air injection test specified by military specification-MIL-R-7726H, supplement 1, is extremely time consuming and not very accurate.

Since aircraft tires are retreaded on average five to seven times and in some cases up to twelve times, any inspection device which is overly expensive and complicated and/or which involves long inspection times, and/or which does not accurately detect different types of defects, will not be commercially viable. There are over 1,400 retreading plants in the United States alone. Therefore, the sheer cost of most prior art inspection equipment makes it impractical to inspect all retreaded tires.

SUMMARY OF THE INVENTION

It is therefore an object of this invention to provide a tire defect detection system and method which accurately detects defects in a tire at a low cost and with short inspection times.

It is a further object of this invention to provide such a tire defect detection system and method which is capable of inspecting 100% of the tire thereby increasing the reliability of the test.

It is a further object of this invention to provide such a tire defect detection system and method which eliminates operator subjectivity.

It is a further object of this invention to provide such a tire defect detection system and method which incorporates many commercial off-the-shelf components.

It is a further object of this invention to provide such a tire defect detection system which is not susceptible to the effects of tire side wall lettering or other molded features.

It is a further object of this invention to provide such a tire defect detection system and method which increases the margin of safety which can be expected from a retreated tire.

This invention results from the realization that tires can be inexpensively and comprehensibly inspected and tested both before and after retreading and even in situ by impacting the tire with an actuator and analyzing the resulting sound wave for evidence of delamination and other faults. A neural network or other non-linear correlator is trained to recognized delaminations and other tire defects based on a number of discriminator quantities computed for each resulting sound wave and to average out non-defect information such as surface lettering, wall thickness, and the like.

This invention features a tire defect detection system comprising a support structure for receiving a tire; an actuator disposed proximate the tire for impacting the tire; a microphone disposed proximate the actuator for receiving a sound wave generated when the actuator impacts the tire; and a computer responsive to the microphone. The computer includes means for calculating a plurality of discriminator quantities from the sound wave, and means for comparing the calculated discriminator quantities with stored discriminator quantities indicative of a defect to determine whether a defect is present in the tire.

The actuator typically includes a solenoid. Further included is a controller for driving the solenoid at an impact time of less than 0.1 seconds. The microphone has a response of approximately 70–15,000 Hz.

The computer preferably includes a routine for performing a FFT transform for each waveform. From this sound wave and the FFT transform, a plurality of discriminator quantities are calculated: the mean value of the amplitude of the FFT transform in each frequency band; the standard deviation of the amplitude of the FFT transform in each frequency band; as the root mean square of the sound wave; the inverse of the autocorrelation time of the sound wave; the average area under each excursion above the standard deviation of the sound wave; the average time between crossings of one standard deviation above the mean; the average time between crossings one standard deviation above the mean and one standard deviation below the mean; the average length of the sound waveform; the average length of the sound waveform above one standard deviation above the mean; and the width of any pulse of the sound waveform which are above one standard deviation above the mean as a discriminator quantity.

The defect detection system further includes means for constructing a defect transfer function based on the calculated discriminator quantities.

The tire defect detection system includes an actuator for impacting the tire; a microphone disposed proximate the actuator for receiving a sound wave generated when the actuator impacts the tire; and a computer responsive to the microphone. The computer is programmed to perform a FFT transform for the sound wave, calculate a plurality of discriminator quantities from the sound wave and the FFT transform, and construct a defect transfer function based on the calculated discriminator quantities to provide an indication of whether a defect is present in the tire.

The method of inspecting tires for defects, in accordance with this invention, includes obtaining a tire with known defects; impacting the tire with an actuator; recording the resulting sound waves; calculating a plurality of discriminator quantities for each sound wave, constructing a defect transfer function based on the calculated discriminator quantities and storing the coefficients thereof. A tire with unknown defects is then impacted with an actuator; the resulting sound waves are recorded; a plurality of discriminator quantities for each sound wave are calculated; and the stored coefficients of the constructed defect transfer function are used to determine whether a defect is present in the tire with unknown defects.

DISCLOSURE OF PREFERRED EMBODIMENT

Other objects, features and advantages will occur to those skilled in the art from the following description of a preferred embodiment and the accompanying drawings, in which:

FIG. 1 is a schematic view of the tire defect system of this invention;

FIG. 2 is a schematic view of the support structure for receiving a tire of the tire defect detection system shown in FIG. 1;

FIG. 3 is a top view of the actuator/microphone fixture of the tire defect detection system shown in FIG. 1;

FIG. 4 is a bottom view of the actuator/microphone fixture shown in FIG. 3;

FIGS. 37–57 are graphs showing the discriminator quantities for each impact at a radius of 9.25 inches on the other side of the tire in accordance with the subject invention;

FIGS. 61–66 are graphs showing the effect of tire to microphone distance on one discriminator quantity in accordance with the subject invention;

FIG. 76 is a flow chart depicting the primary steps associated with the tire defect detection method of the subject invention after the neural network is trained; and FIG. 77 is a schematic view of a fully automated tire defect detection system in accordance with the subject invention.

Figure 6:
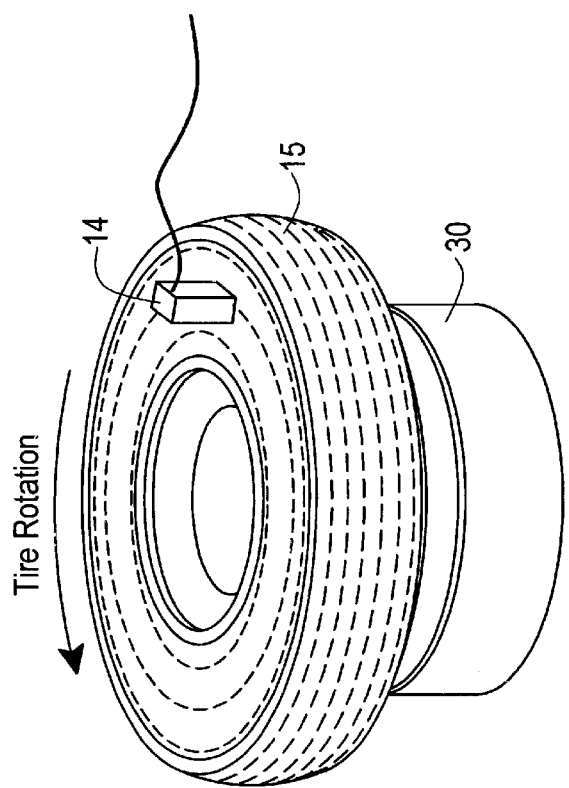
FIG. 6 is a schematic view depicting the method of detecting defects in accordance with the subject invention.

Tire defect detection system 10, FIG. 1 includes support structure 12 for tire 15, actuator/microphone fixture 14 disposed over tire 15 via arm 18 which is mounted on base stand 20, computer 22 connected to monitor 24, and controller 26.

Support structure 12, FIG. 2, includes tire support 30 rotatably mounted on spindle 32 received in support base 34 filled with a vibration damping material such as concrete. Spindle 32 could be motor driven in an alternative embodiment. Spindle 32 is capable of supporting a 300 pound tire which is the weight of the largest aircraft tire in common use today.

Base stand 20, FIG. 1 includes heavy cast iron base 36 mounted on three self-leveling rubber padded feet as shown. Bracket 38 interconnects aim 18 and base stand 20 to provide height and angle adjustment of actuator/microphone fixture 14 with respect to tire 15.

Actuator/microphone fixture 14, FIGS. 3 and 4 includes solenoid 40 with hammer return spring 42 such as an Electro-Mechanisms model SP-100, 6 volt, high temperature 180° C. coils. Microphone 44, FIG. 4, for example, a Radio Shack Optimist catalog no. 33-3013 with a flat response from 70–15,000 Hz, is mounted proximate hammer 46 of solenoid 40 but physically isolated therefrom by two independent sets of rubber grommets to insulate microphone 44 from any solenoid vibrations.

Figure 5:
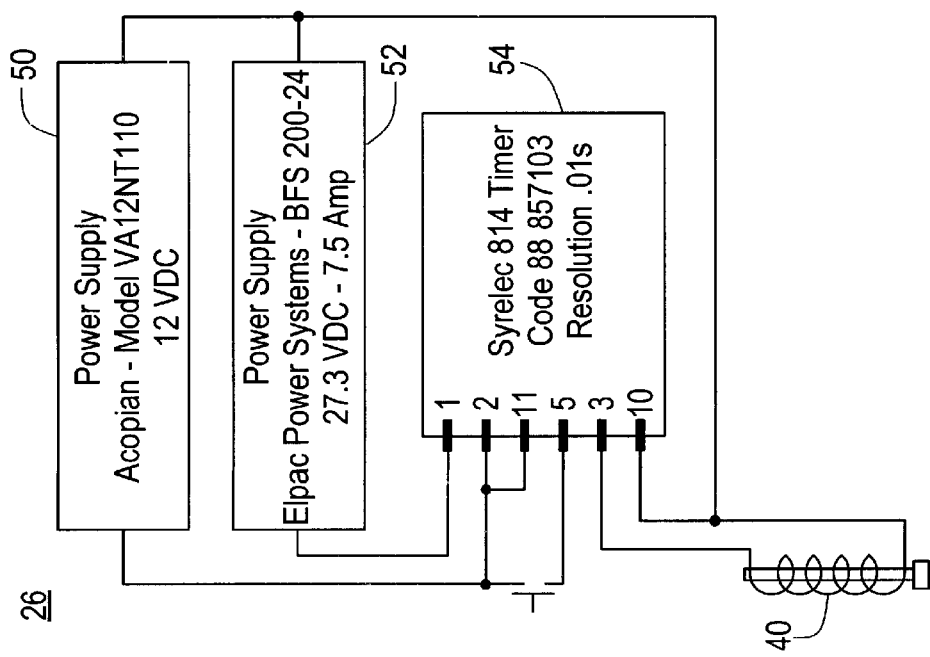
FIG. 5 is a block diagram of the controller of the tire defect detection system shown in FIG. 1.

Solenoid 40 is connected to controller 26, FIG. 5, which provides an applied voltage of 24 volts to solenoid 40. Controller 26 includes an Acopian model ZA12NT110 12 volt DC power supply 50, Elpac power systems-BFS200-24 (27.3 VDC-7.5 amp) power supply 52, and Syrelec 814 timer 54 connected as shown to provide an actuation time of between 0.01 to 0.03 seconds. Experimentation proved that an actuation time of 0.03 seconds was optimal.

Microphone 44 is connected to computer 22, FIG. 1 programmed to 1) perform a FFT transform for each sound wave recorded by microphone 44, 2) compute a number of "discriminator quantities" based on each sound wave and the FFT transform, and 3) construct a defect transfer function based on the discriminator quantities discussed infra.

Figure 7:
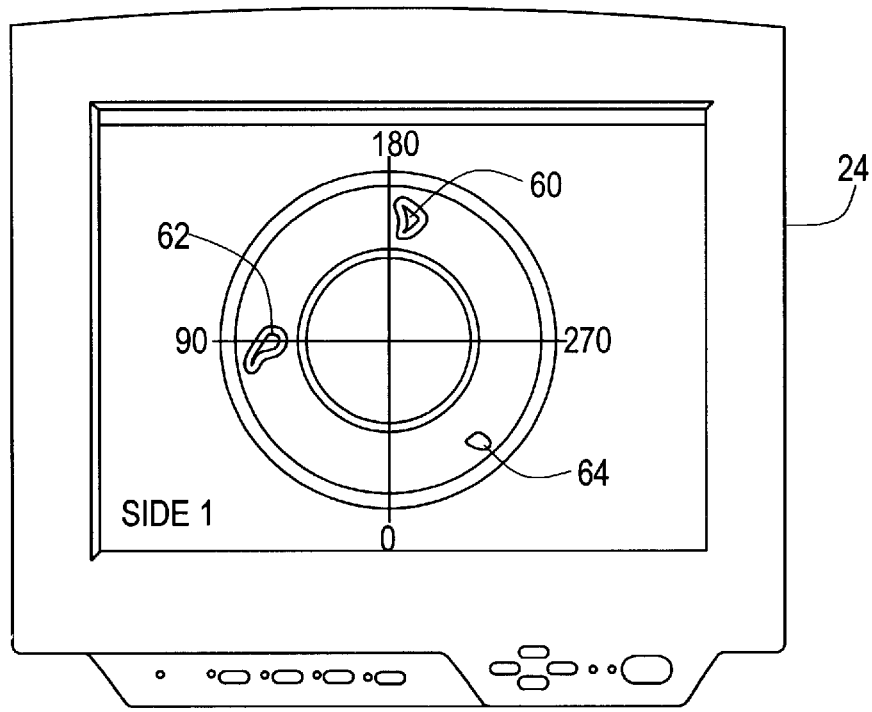
FIG. 7 is a front view of the monitor of the tire defect detection system shown in FIG. displaying an image of the tire wall and defects.

In general, tire 15, FIG. 6 is rotated and the solenoid is actuated for 0.03 seconds every 10° of tire rotation at a radius of 7.25 inches, 8.25 inches, and 9.25 inches of each side wall of the tire and also on the tire tread area. After computer 22, FIG. 1, completes its processing, defects 60, 62, and 64, FIG. 7 are displayed on monitor 24. In this example, the defects were delaminations and their approximate size and location are displayed to the user. Other defects such as cuts and the like, however, can also be detected in accordance with this invention.

Figure 8:
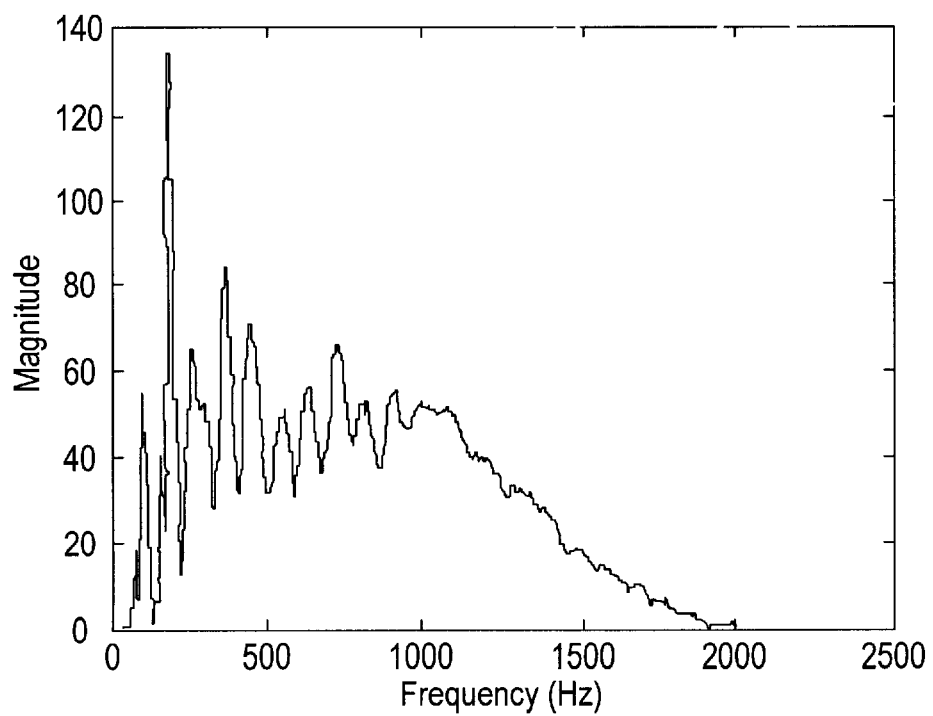
FIG. 8 is a graph of the FFT of the sound wave analyzed in accordance with the subject invention.
Figure 9:
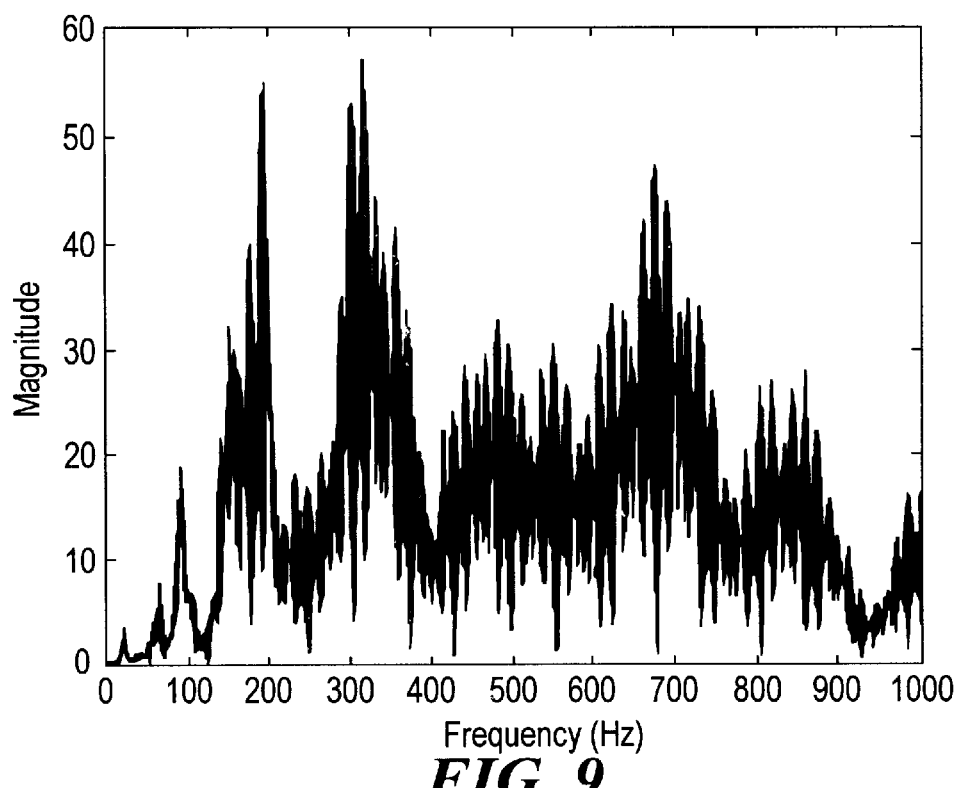
FIGS. 9 and 10 are graphs showing details of the FFT transform of the sound wave shown in FIG. 8.
Figure 10:
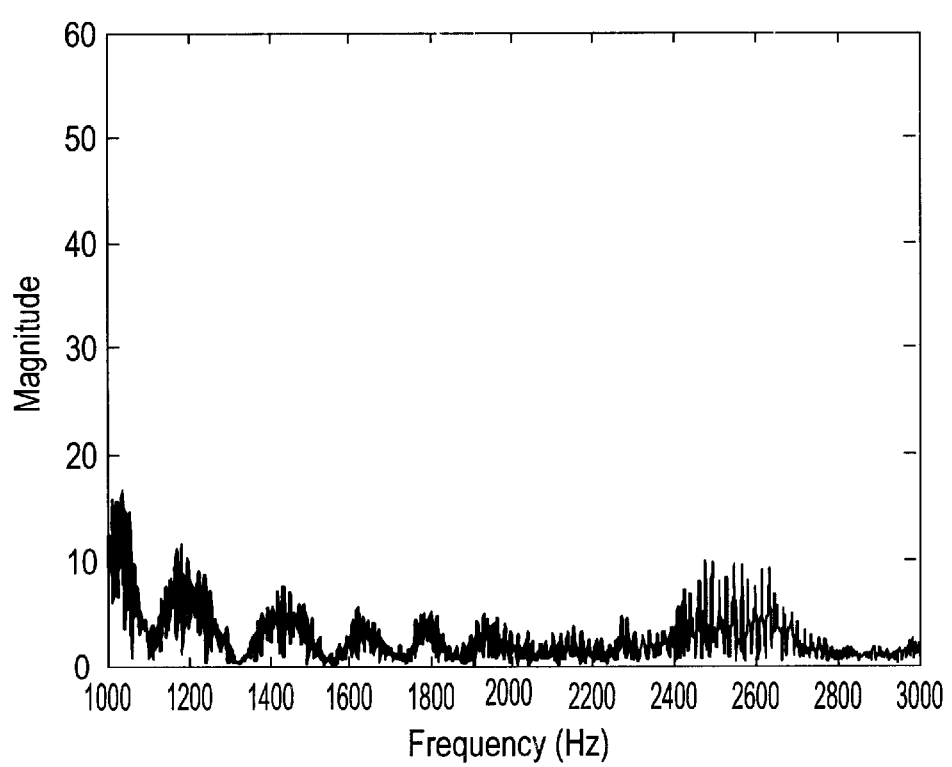
Figure 11:
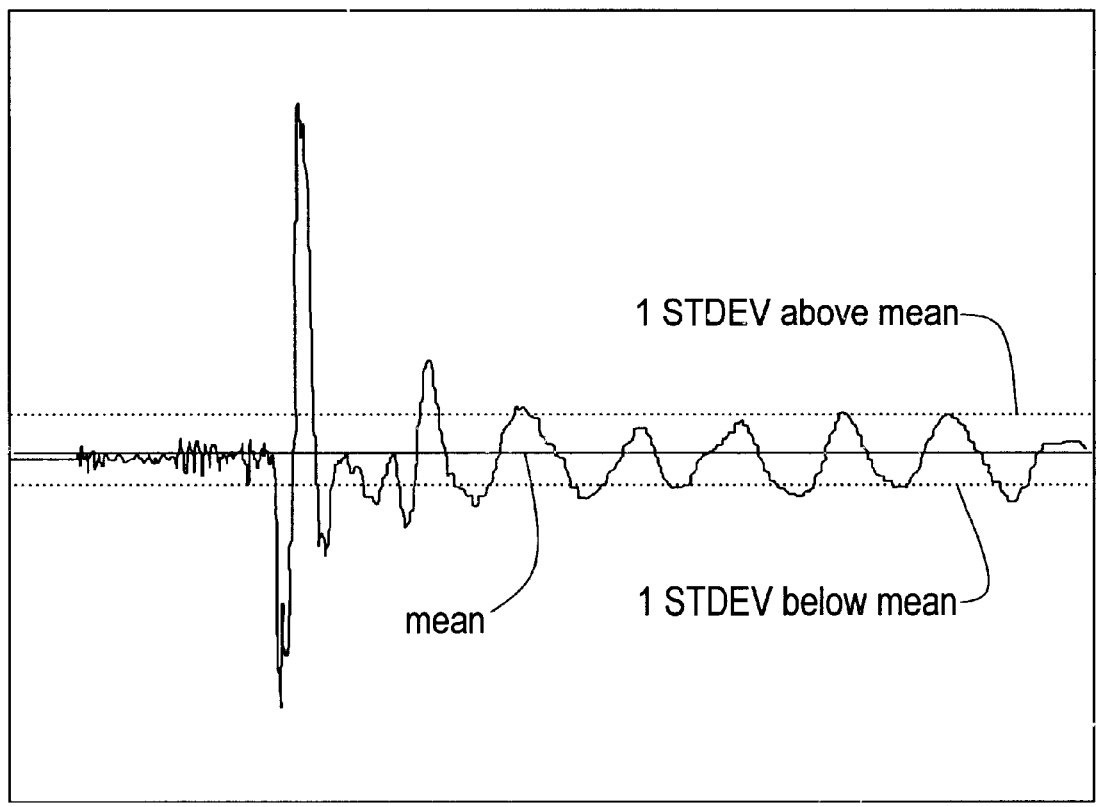
FIG. 11 is a graph showing the calculation of the standard deviation discriminator quantity calculated from the FFT transform of FIGS. 9–10 in accordance with the subject invention.

The processing of computer 22, FIG. 1, is explained in relation to FIGS. 8–76. Microphone 44, FIG. 4, delivers to the computer a waveform as shown in FIG. 11 for each strike of the solenoid hammer on the tire. The computer is programmed to compute a moving window Fourier Transform, sometimes referred to as an Overlapping Gabor Transform representative of the time evolution of the response spectrum as shown in FIGS. 9 and 10. As shown, most of the resulting energy is partitioned into six definite frequency bands: 120 Hz-250 Hz, 250 Hz-400 Hz, 400 Hz-800 Hz, 800–1000 Hz, 1 kHz-2 kHz, and 2 kHz-3 kHz. When a delamination is present in the tire, energy shifts from one band to another. By monitoring the relative energy levels between defective and non-defective areas in each band, the defects in the tire can be detected and located.

From the FFT transform of each wave and from the waves themselves, a number of discriminator quantities are computed as discussed below.

The first six discriminator quantities (M1–M6) are the mean value of the amplitude of the FFT transform in each of the six identified bands. These values are indicative of the elasticity of the tire under test. The next six discriminator quantities (SD1–SD6) are the standard deviation of the amplitude of the FFT transform in each of the six bands. These values are indicative of the peaks within each band or the Q of the material.

The root means square discriminator quantity (RMS) is calculated as:

$$\frac{1}{N} * \sqrt{\sum_{i=1}^{N} (X_i)^2} \qquad (1)$$

in the time domain where N is the number of points in the sample, and X is the sample point on the wave in the time domain. This discriminator quantity is most sensitive to the tire's initial response impact.

Another discriminator quantity is the standard deviation (STDEV) of the points on the waveform in the time domain. Once this quantity is calculated, lines are defined as one standard deviation above and below the mean as shown in FIG. 11. Many other discriminator quantities are related to this defined interval.

The slope as a discriminator quantity refers to the inverse of the characteristic autocorrelation time. This is the time scale during which the signal loses linear correlation, and is suggestive as a measure of the rate of mixing in a given process. The auto correlation $C_{xx}(\tau)$ is the integral over all time of the signal x(t) multiplied by the time-delayed version of the signal x (t–τ). For no time delay, (τ=0), the autocorrelation thus equals:

$$\overline{nx^2} \qquad (2)$$

For large τ values, the auto correlation approaches $$\overline{nx}^2 \qquad (3)$$

where n is the number of readings in the record.

Figure 12:
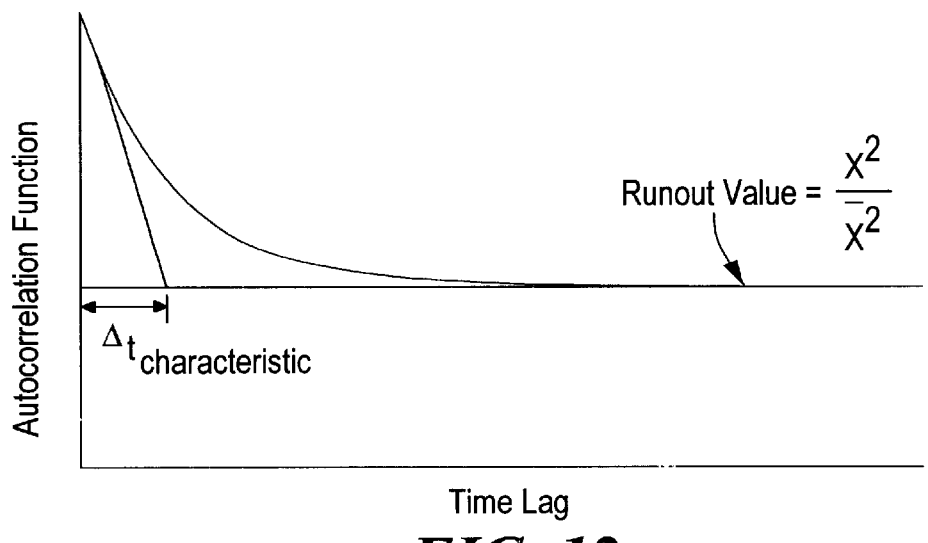
FIG. 12 is a graph showing a typical autocorrelation function calculated in accordance with the subject invention.

As shown in FIG. 12, the characteristic autocorrelation time is the time intercept of a line at the initial downward slope of the autocorrelation curve with the run out value $\Delta t_{characteristic}$) given by:

$$\Delta t_{characteristic} = \frac{\sum x^2 - N_x^{-2}}{\sum x^2 - \Sigma[x_i(x_{i+j})]} \qquad (4)$$

Normalization usually sets the initial value to "1" so that the initial slope is $$SLOPE = \frac{1}{\Delta t_{CHARACTERISTIC}} \qquad (5)$$

Figure 13:
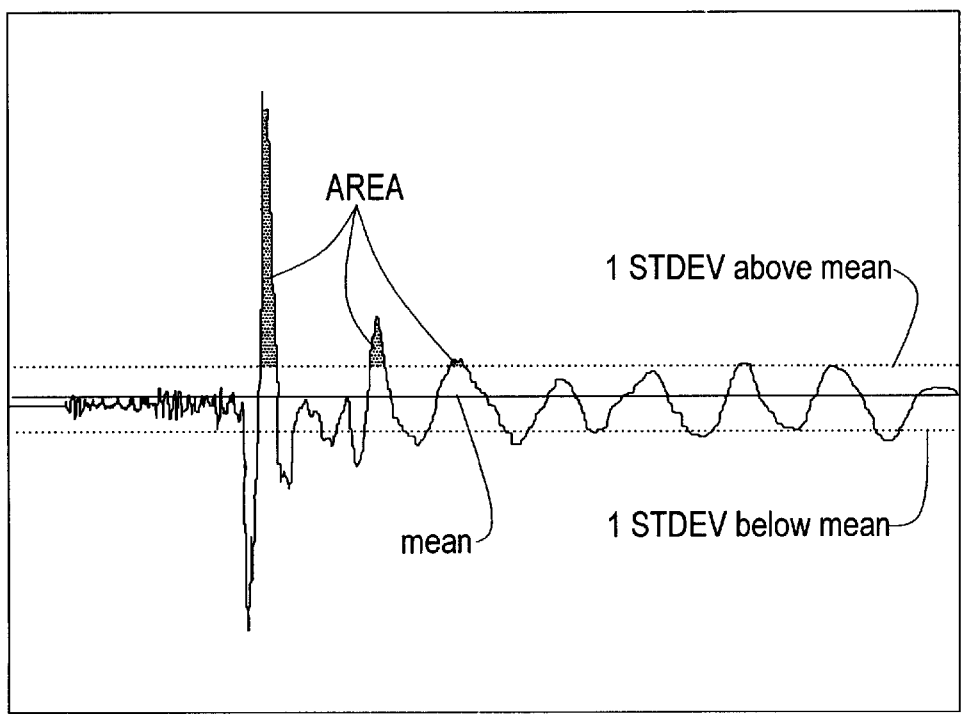
FIG. 13 is a graph showing the calculation of the area discriminator quantity in accordance with the subject invention.

The area discriminator quantity (AREA) is the average area under each excursion above the first standard deviation line as shown in FIG. 13 and is indicative of the damping weight of the waves in the tire and hence the material properties of the tire.

The HCROSS discriminator quantity is a tally of the total number of times the signal rises above the upper standard deviation line. The HLCROSS discriminator quantity is the tally of the number of times the signal rises above the standard deviation line and then continues by falling below the lower standard deviation line. It is believed that these quantities describe the decay rate of the signal by counting the large amplitude excursions, but in the final analysis these two discriminator quantities were not used as values indicative of delaminations. In addition, the RMS and the STDEV values seem to carry the same information and hence only one value, namely the RMS value, is used in the preferred embodiment.

Figure 14:
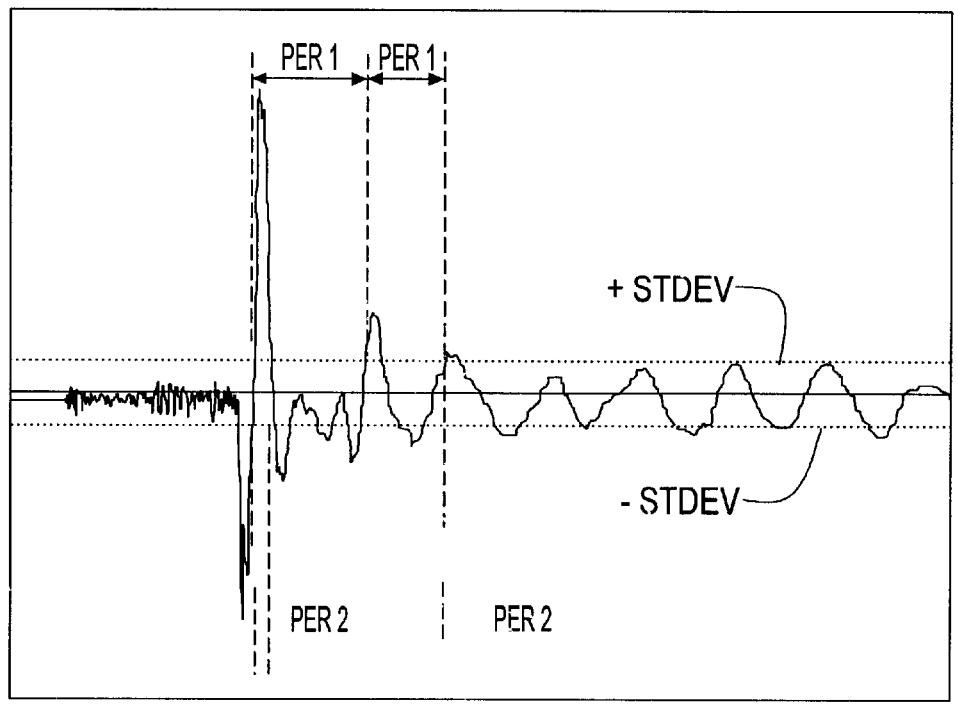
FIG. 14 is a graph showing the period measurement discriminator quantities calculated in accordance with the subject invention.

The PER 1 and PER 2 discriminator quantities are period measurements parallel to the crossing measurements described above. PER 1 corresponds to HCROSS in that measures the average time between rising crossings of the upper standard deviation line. PER 2 corresponds to HLCROSS in that it measures the average time between the upper standard deviation line and lower standard deviation line crossings as shown in FIG. 14.

The LEN 1 and LEN 2 discriminator quantities are lengths derived from the length of the signal. If the signal is imagined to be stretched out flat, a signal with many high frequency, large amplitude information will stretch out farther than one with a smooth texture. Thus, these two discriminator quantities contain information about the high frequency content of the signal. LEN 1 is the length of the overall contour of the signal from the start to end. LEN 2 is the average length of the contour of the signal that just lies above the upper standard deviation line. This value contains specific information about the high frequency content of the large amplitude excursions.

Figure 15:
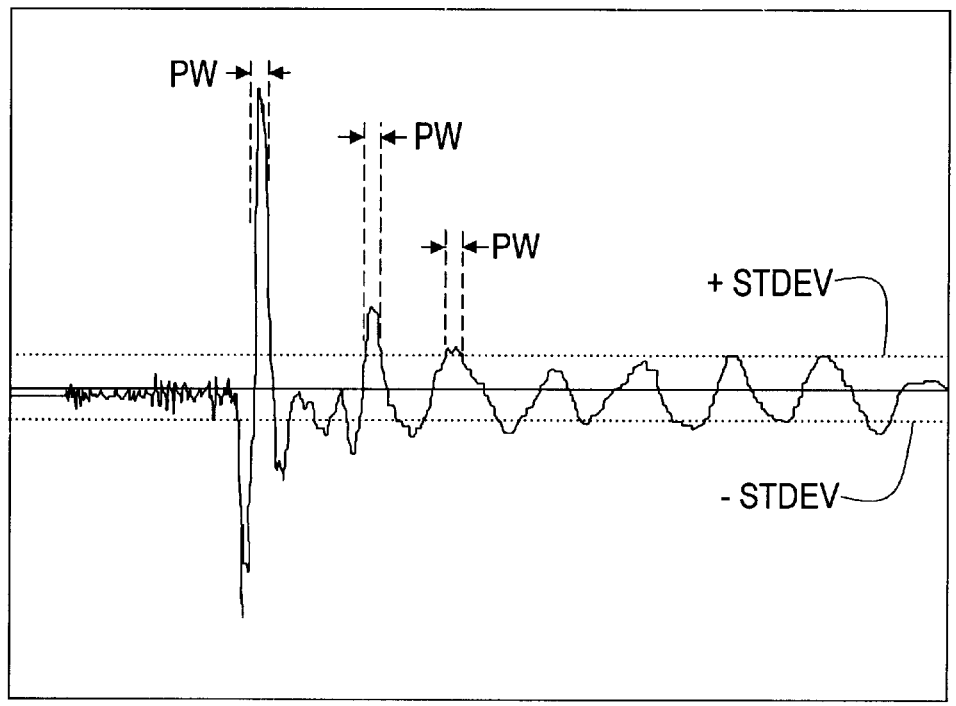
FIG. 15 is a graph showing the average pulse width discriminator quantities of the subject invention.
Figure 16:
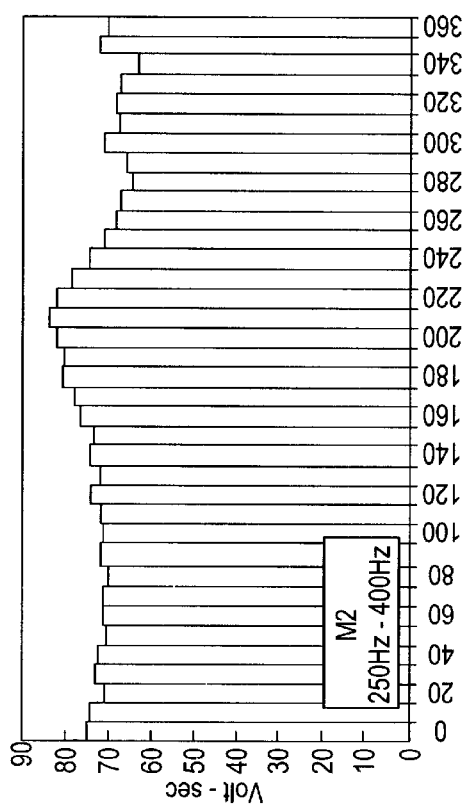
FIGS. 16–36 are graphs showing the actual discriminator quantities for each impact of the tire defect detection system of this invention at a radius of 7.25 inches on one side of a tire being inspected.
Figure 17:
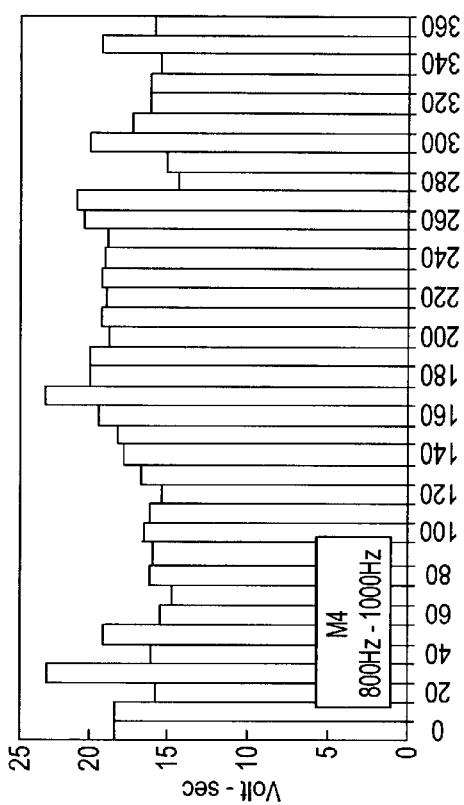
Figure 18:
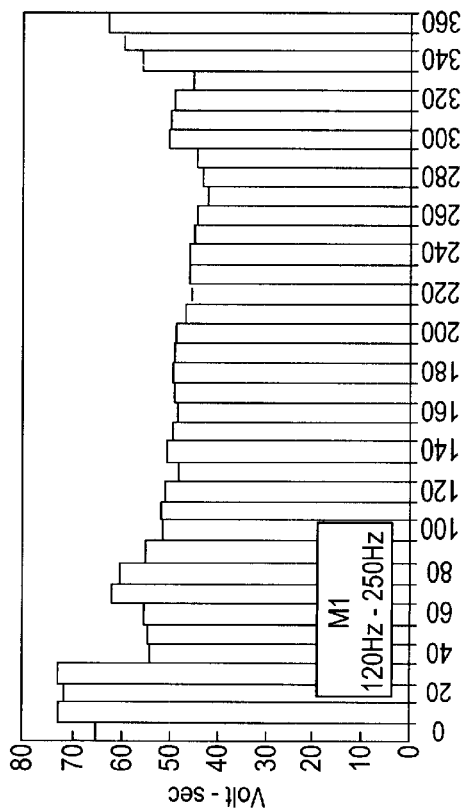
Figure 19:
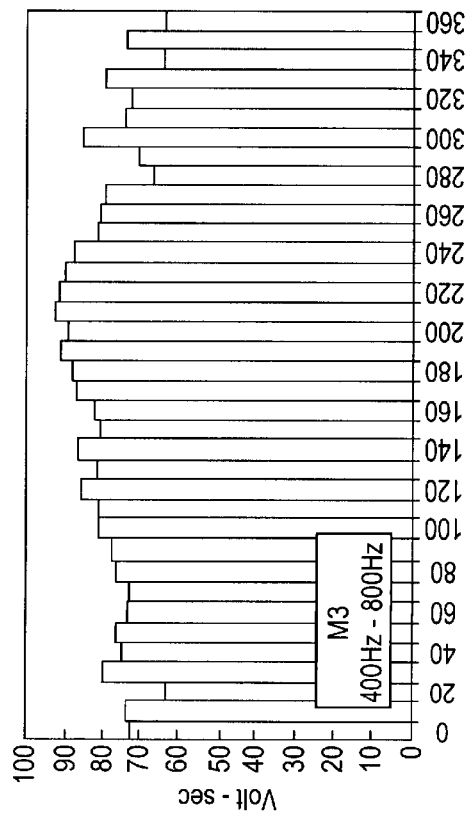
Figure 20:
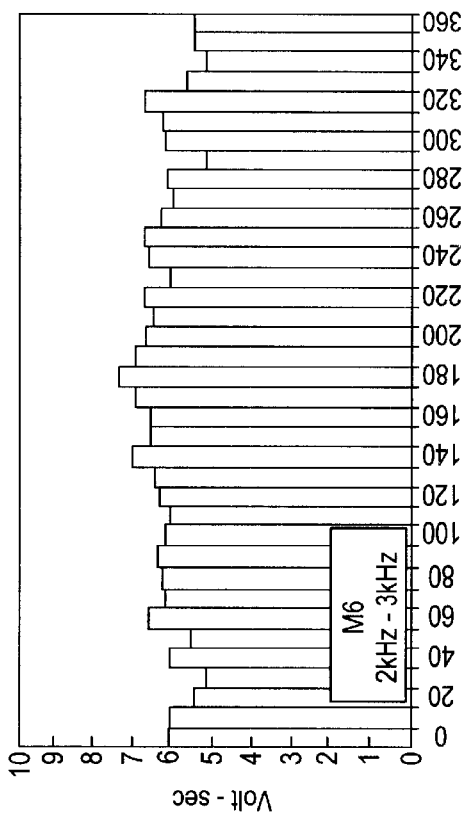
Figure 21:
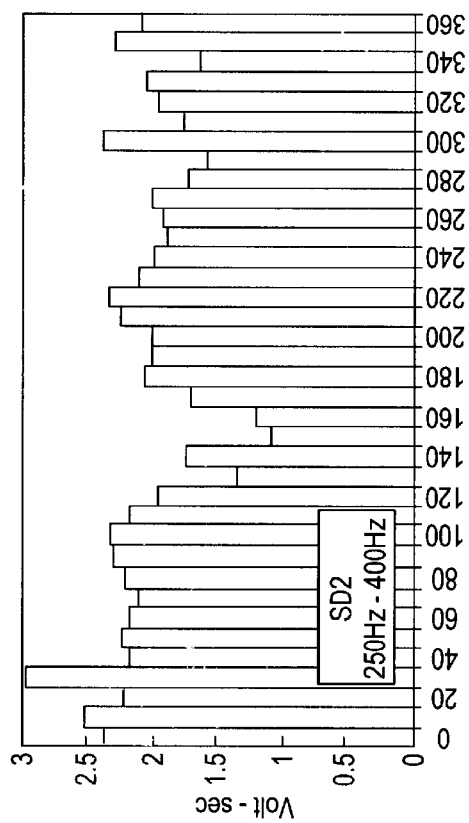
Figure 22:
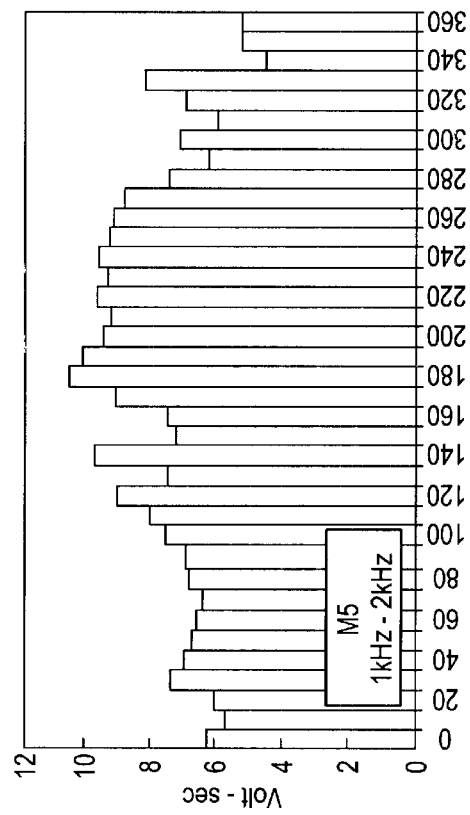
Figure 23:
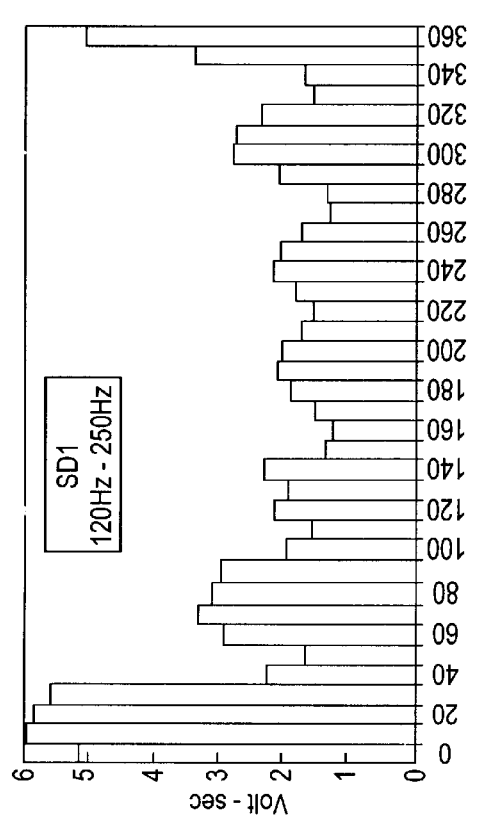
Figure 24:
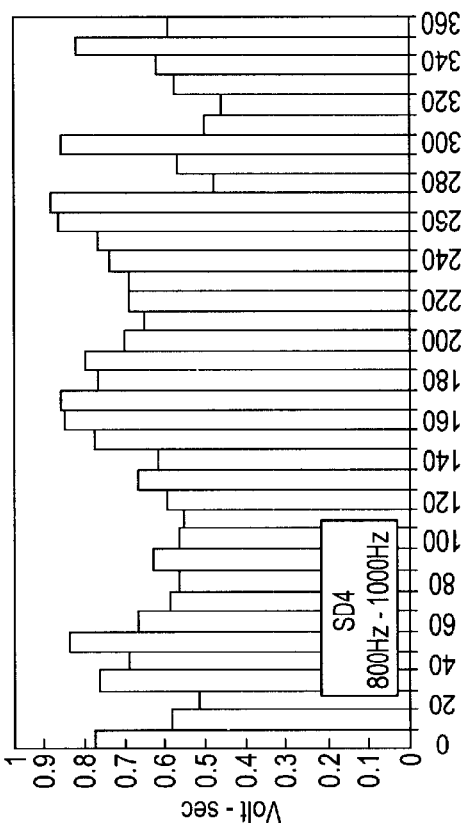
Figure 25:
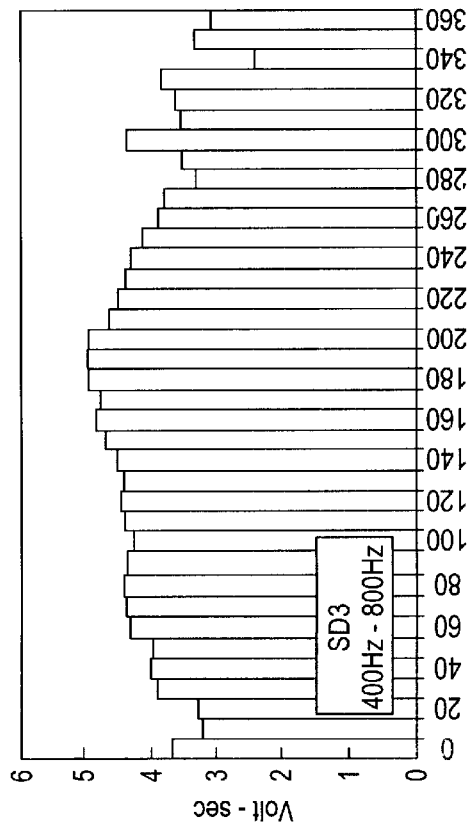
Figure 26:
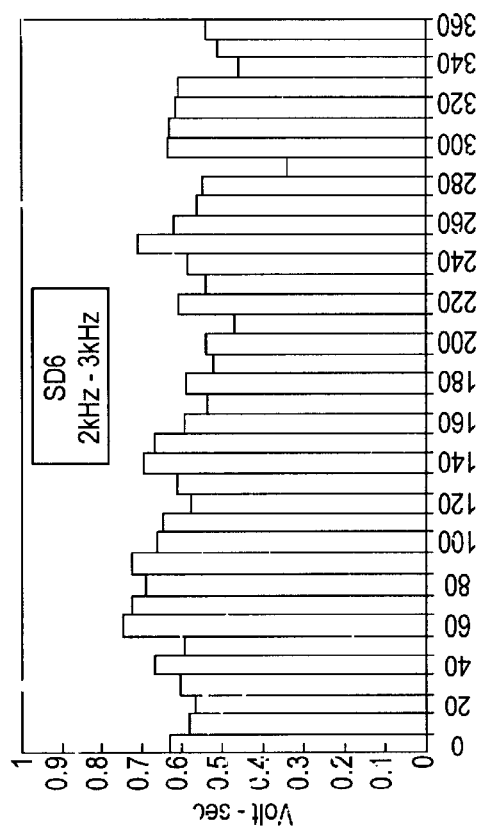
Figure 27:
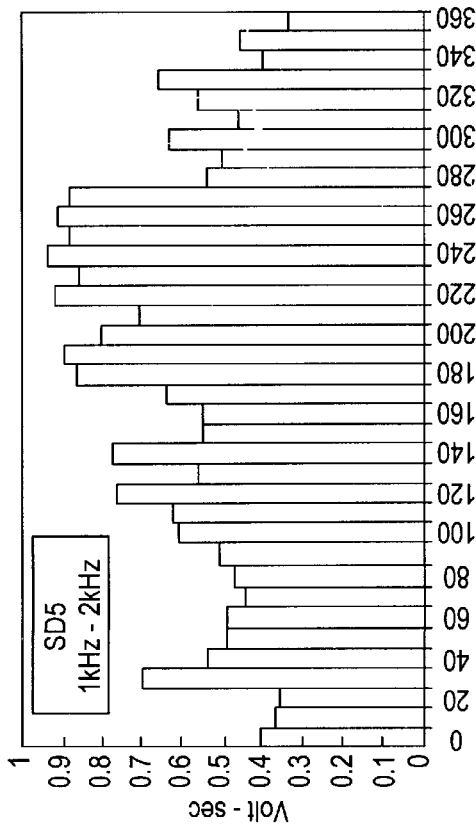
Figure 29:
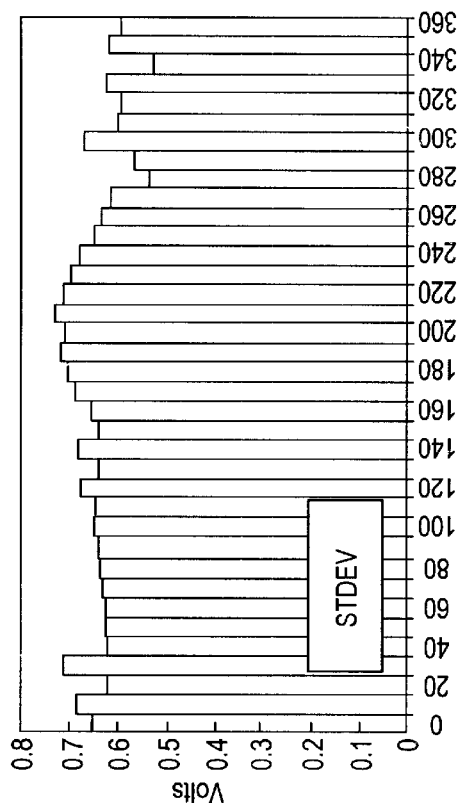
Figure 28:
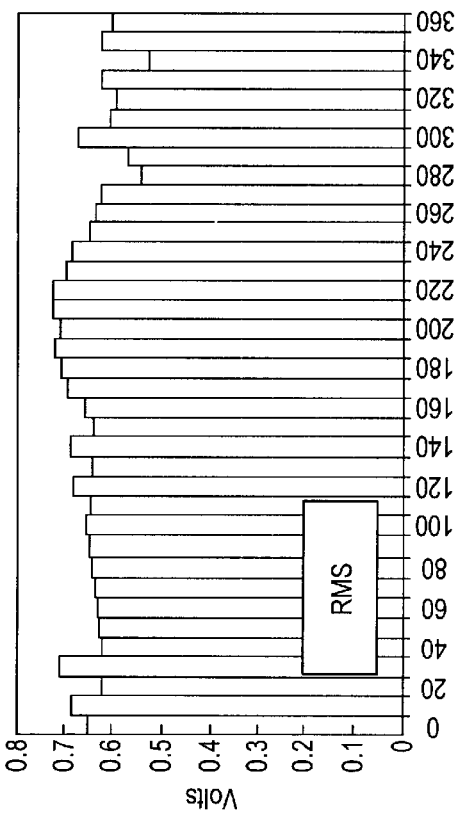
Figure 31:
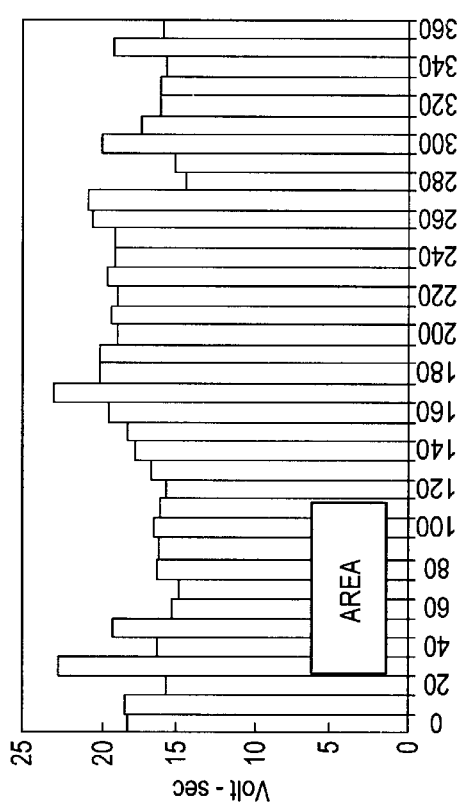
Figure 30:
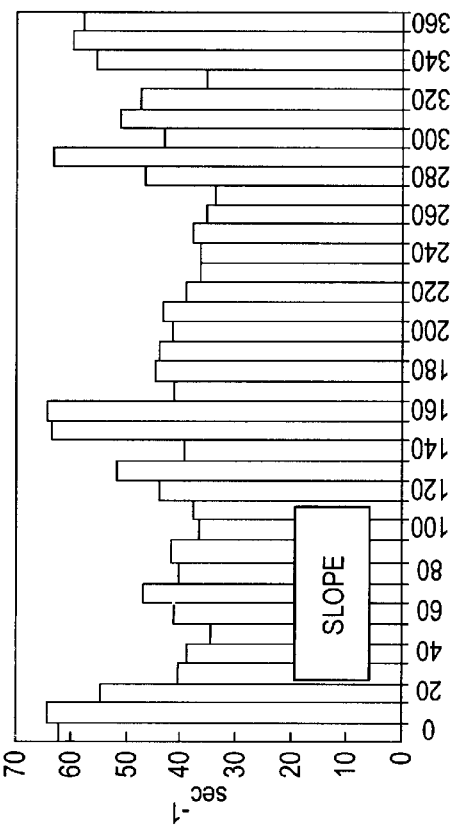
Figure 32:
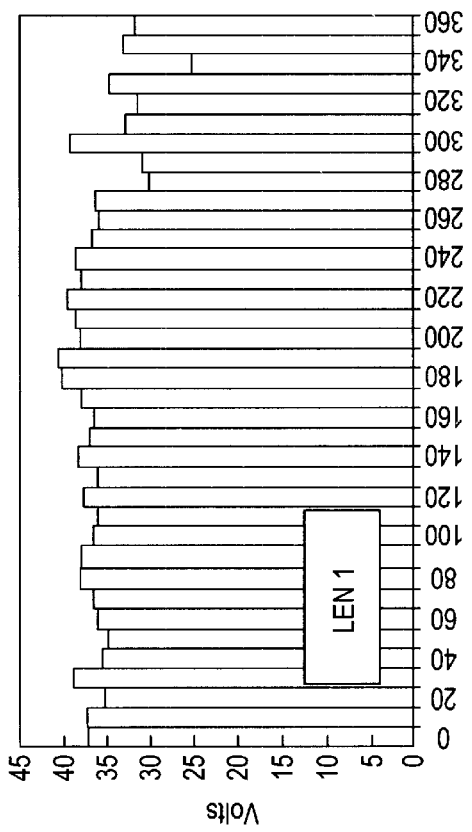
Figure 34:
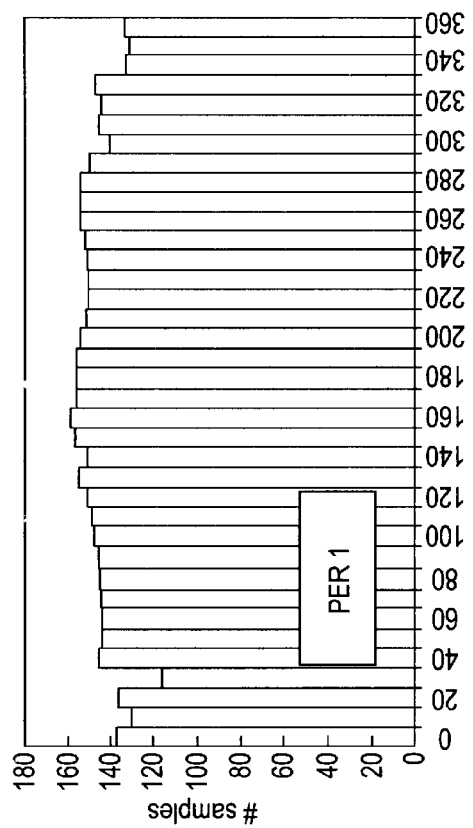
Figure 33:
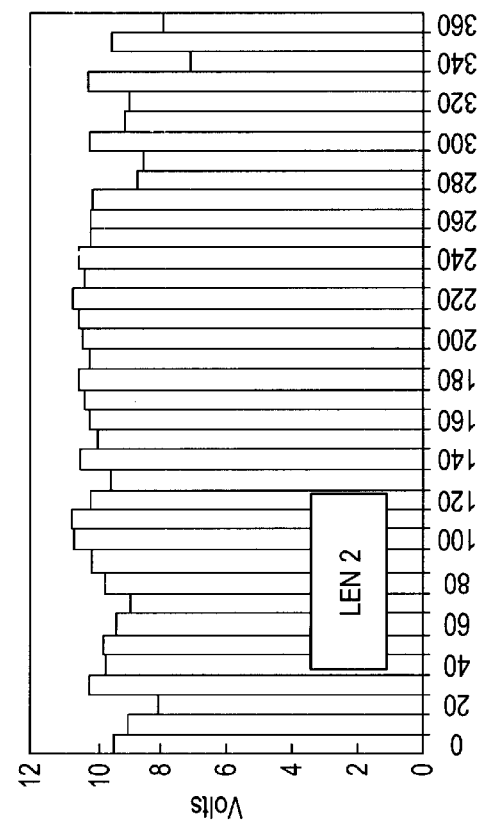
Figure 35:
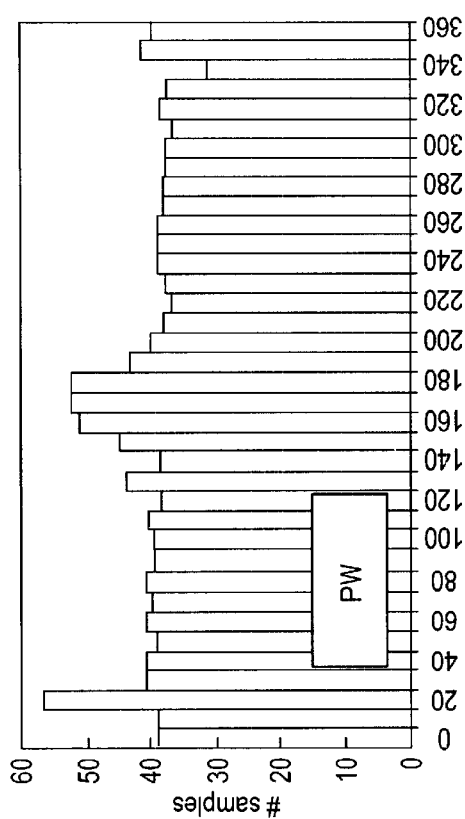
Figure 36:
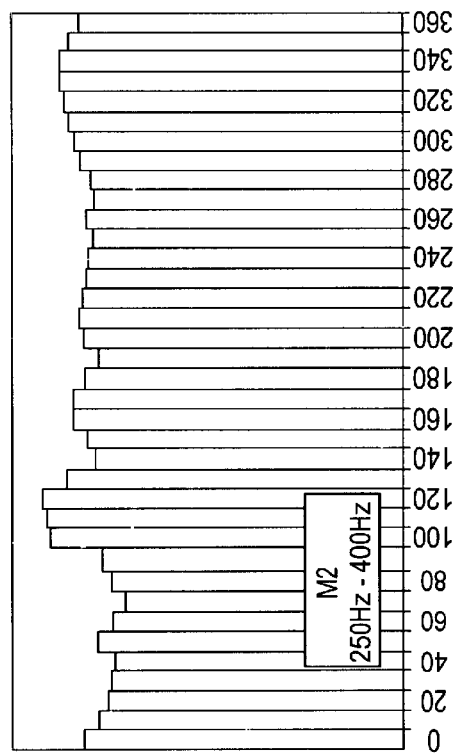
Figure 37:
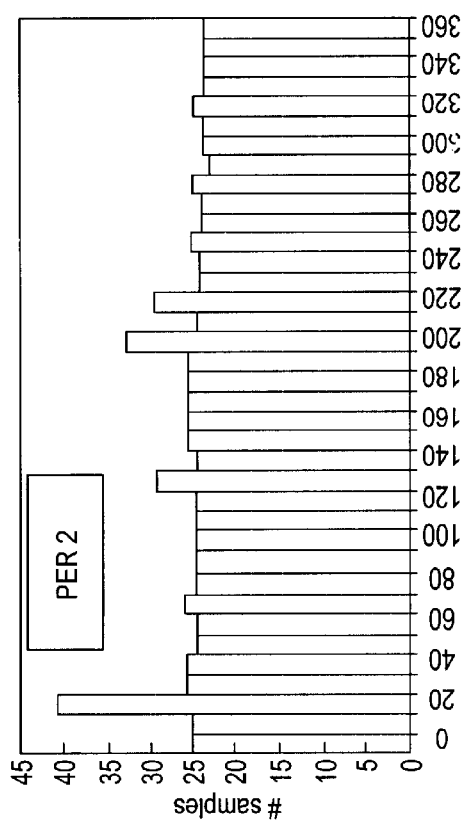
Figure 38:
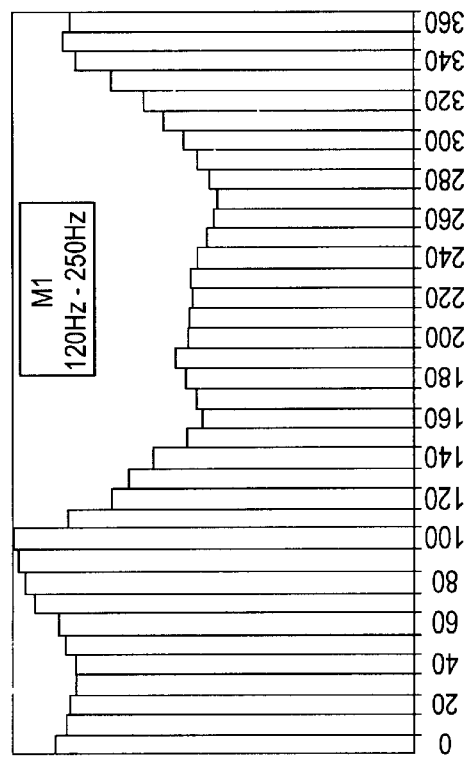
Figure 39:
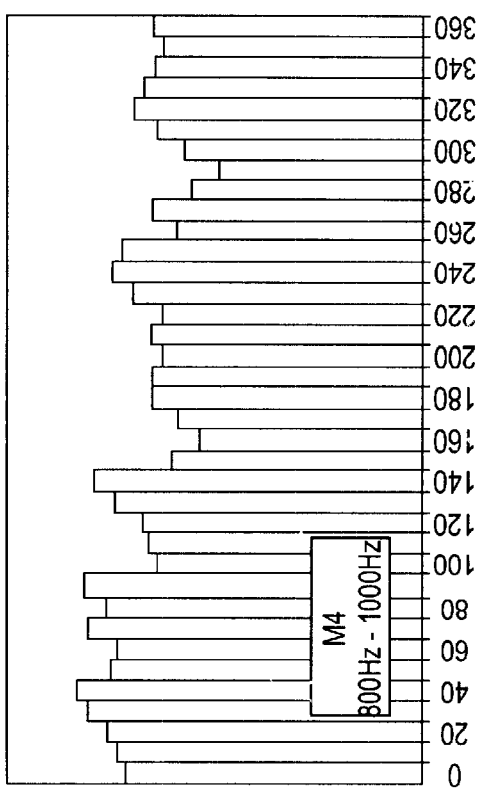
Figure 42:
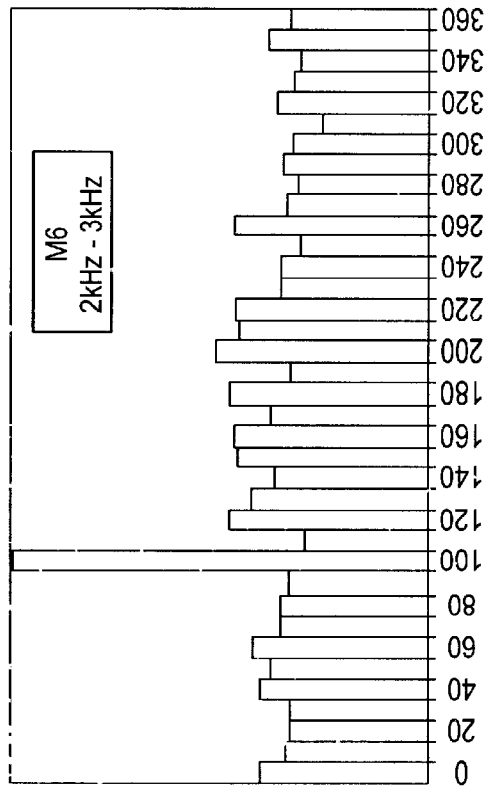
Figure 46:
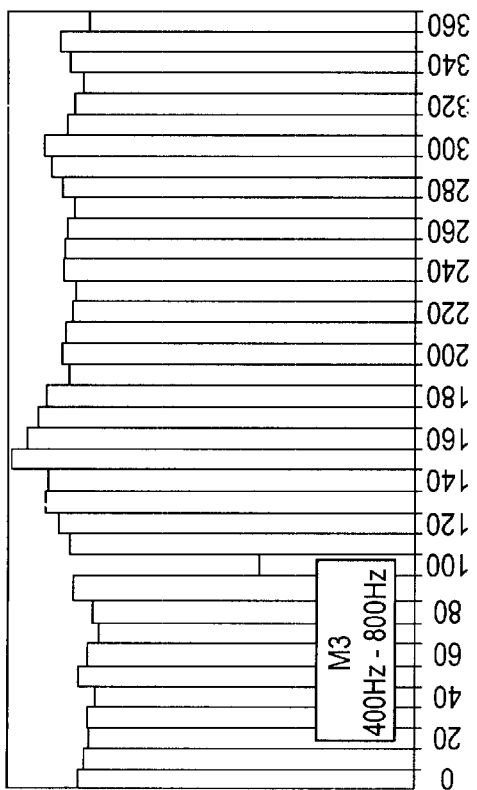
Figure 41:
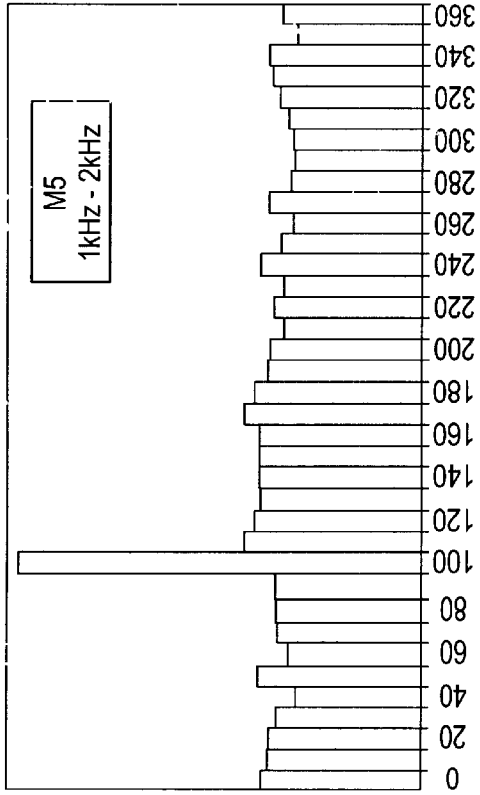
Figure 43:
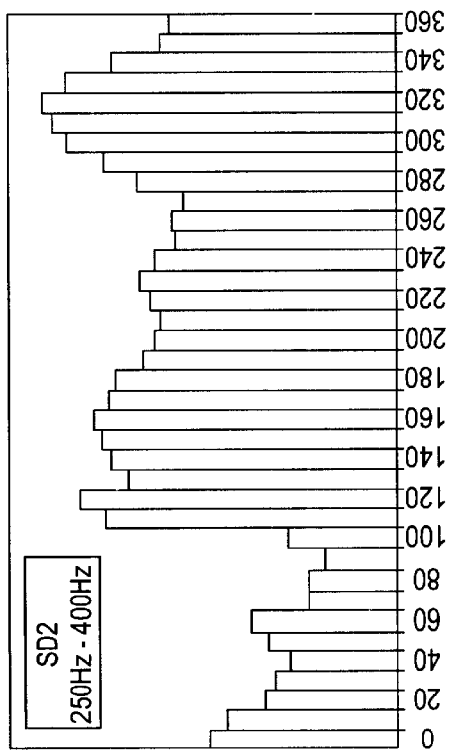
Figure 44:
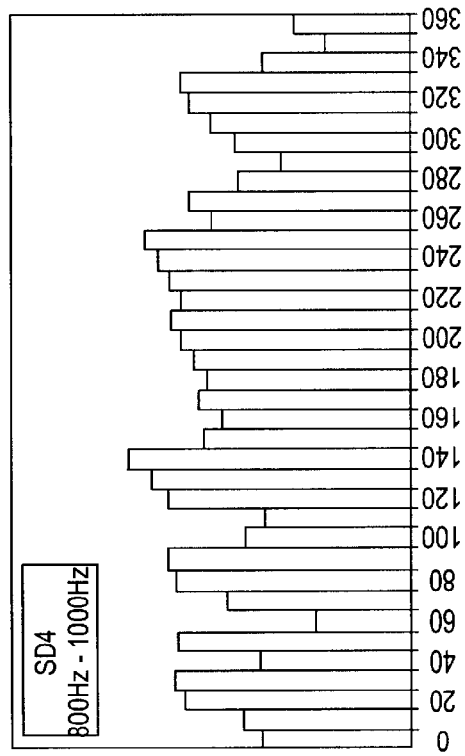
Figure 45:
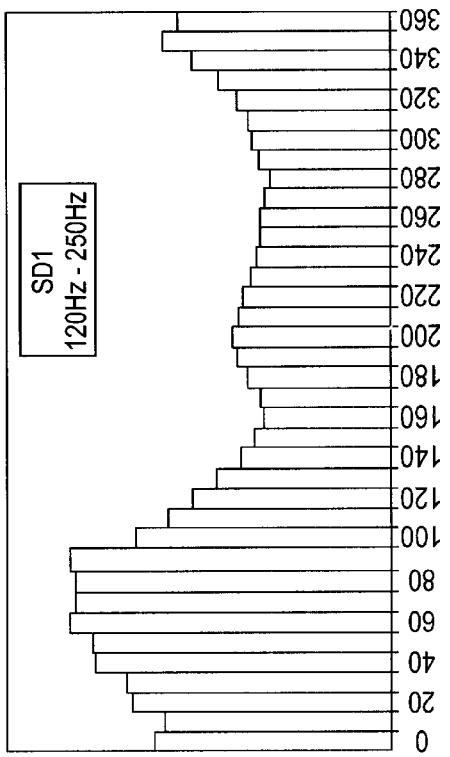
Figure 46:
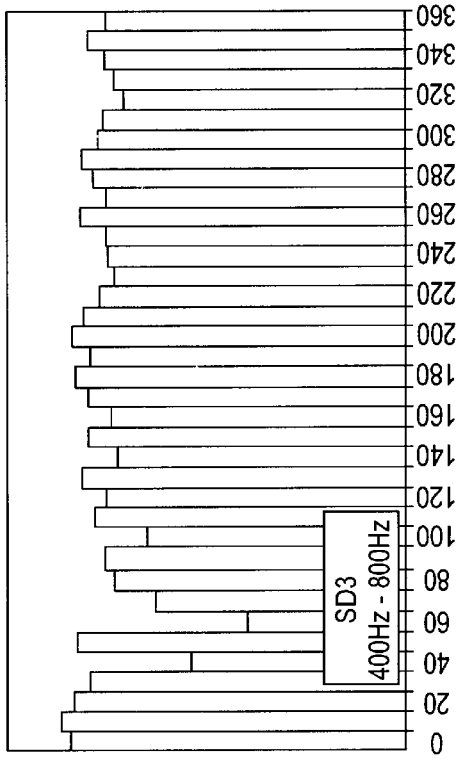
Figure 47:
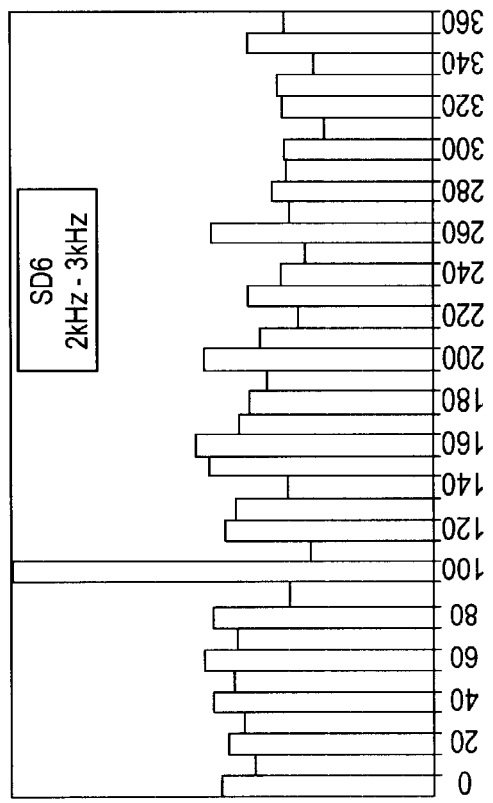
Figure 48:
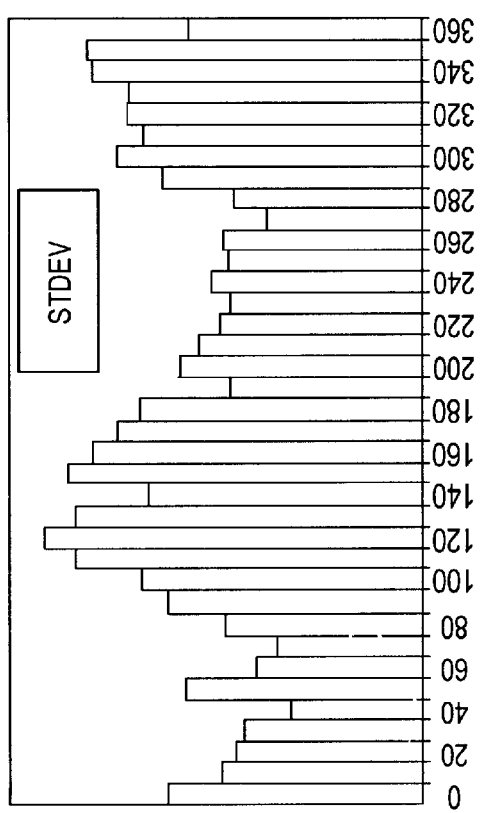
Figure 49:
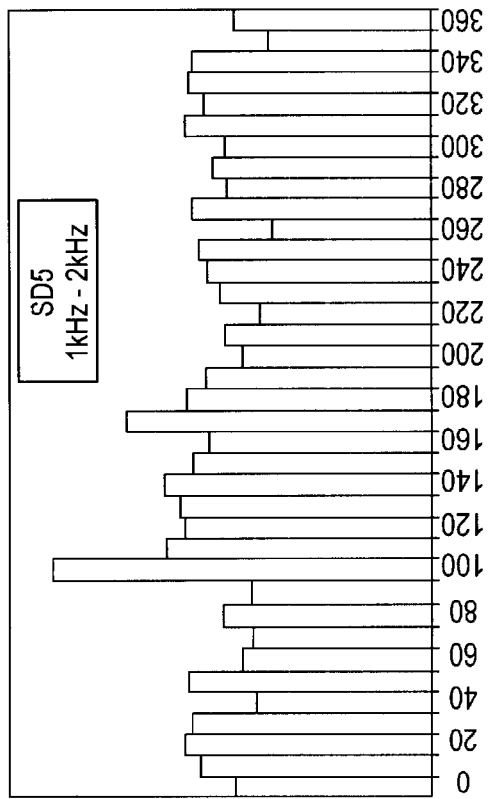
Figure 50:
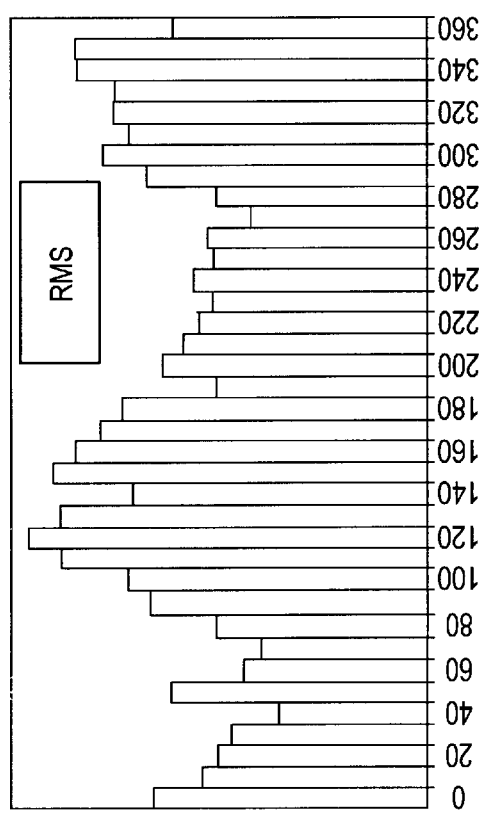
Figure 51:
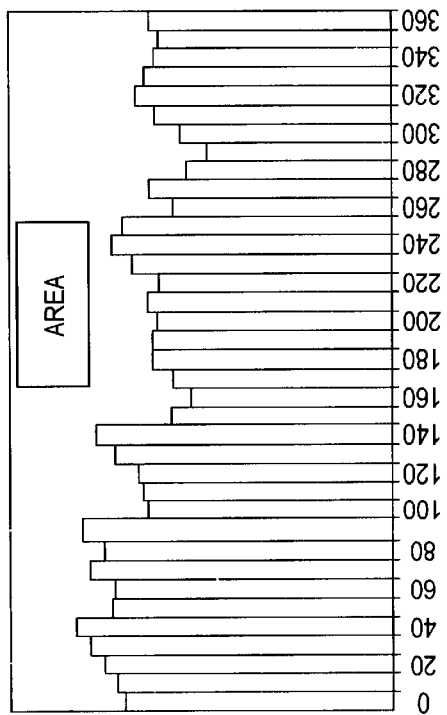
Figure 52:
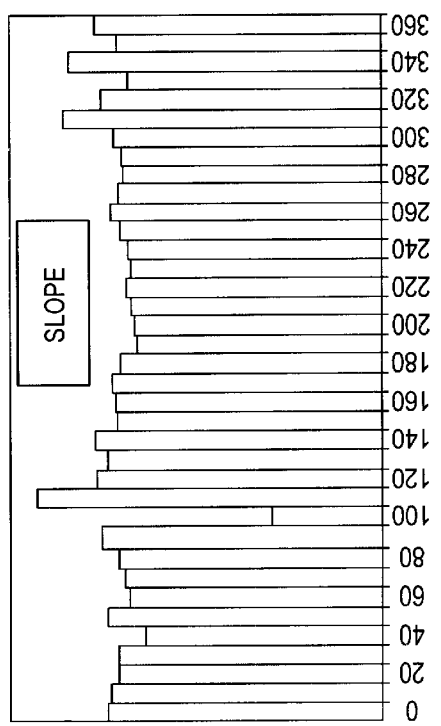
Figure 53:
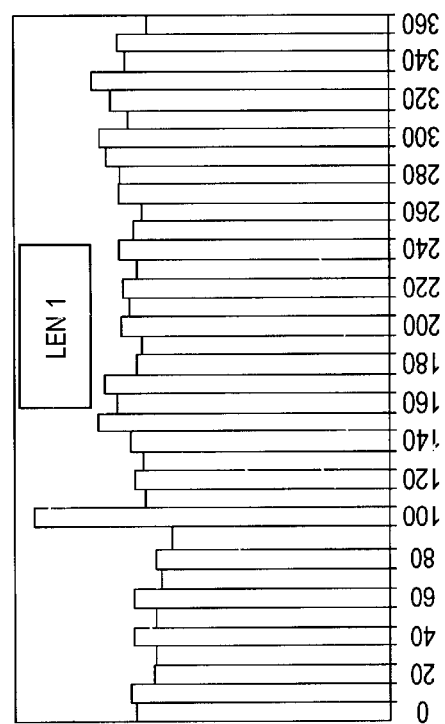
Figure 55:
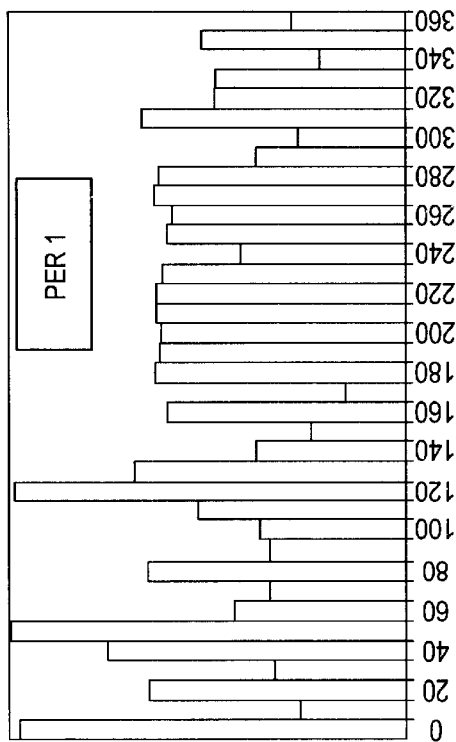
Figure 57:
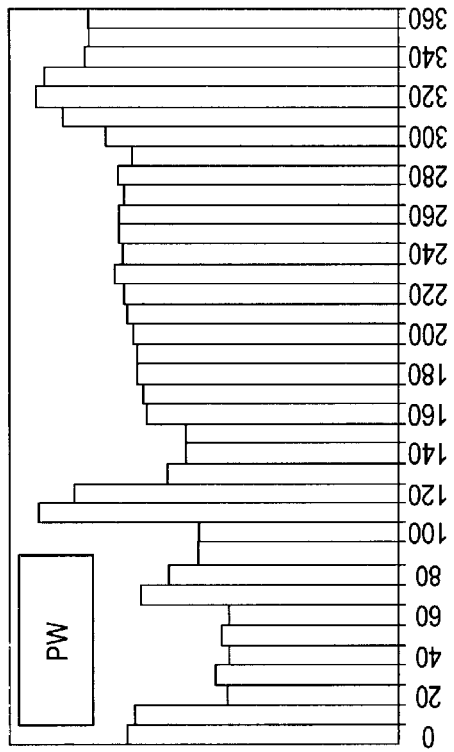
Figure 54:
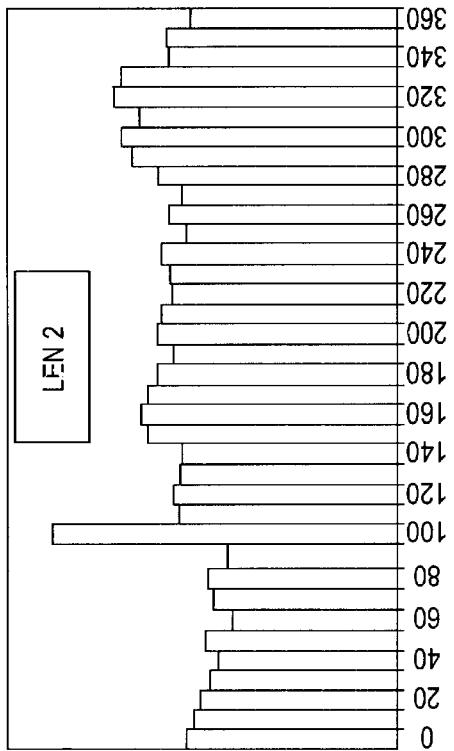
Figure 56:
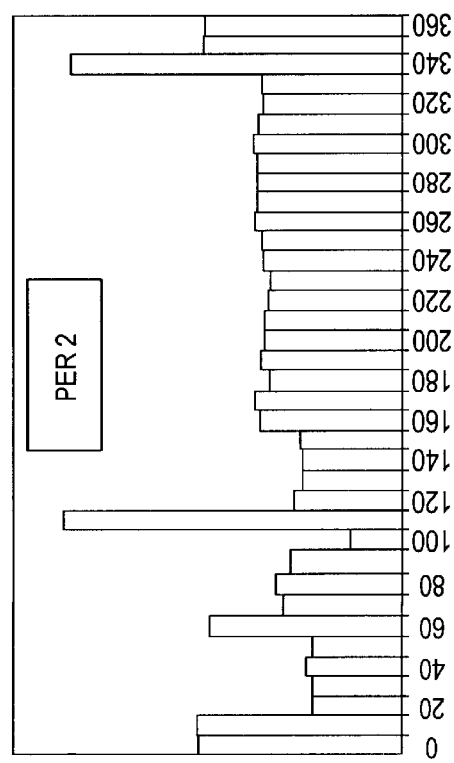

PW is the discriminator quantity which represents the average pulse width of peaks that rise above the upper standard deviation line. PW is measured in time steps and is measured at the upper standard deviation line as shown in FIG. 15. This quantity contains information about the bulk response of the tire to the initial impact of the solenoid.

Figure 58:
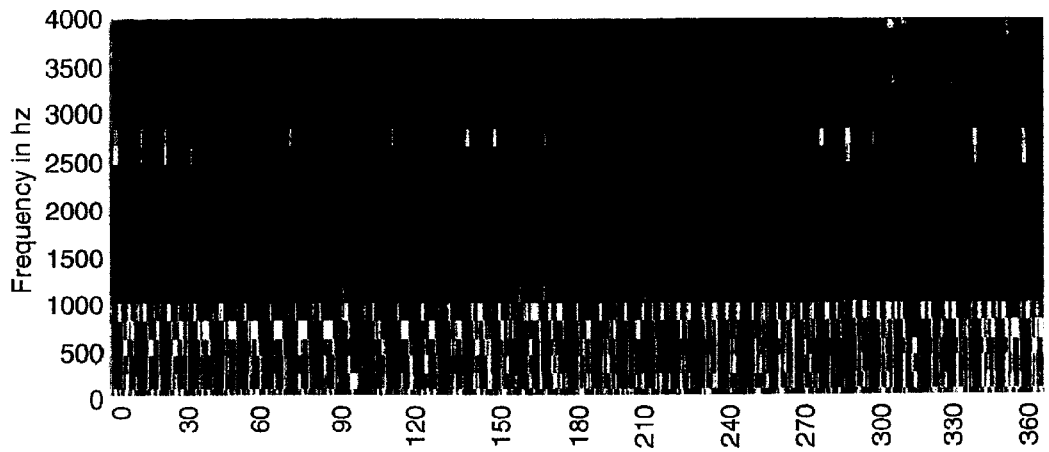
FIGS. 58–60 are graphs depicting the impact frequency response of one side of a tire under inspection at a radius of 7.25 inches, 8.25 inches, and 9.25 inches respectively.
Figure 59:
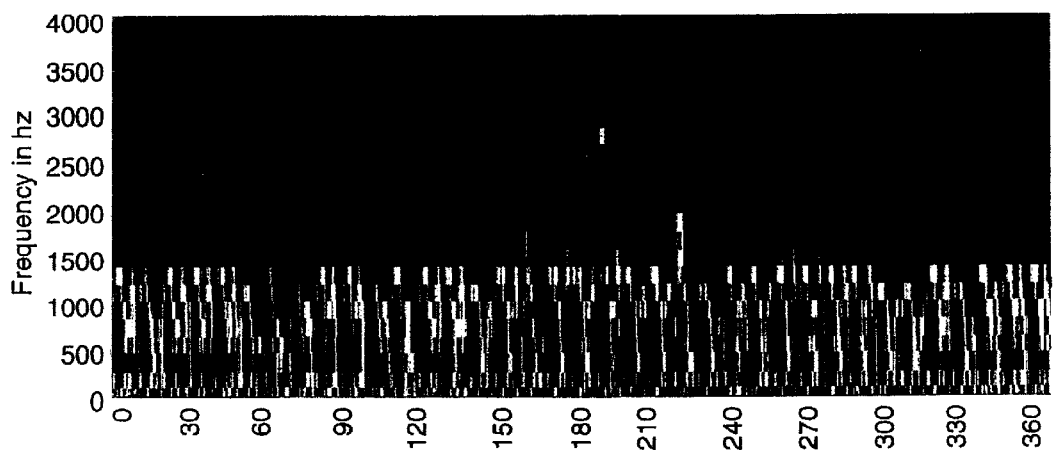
Figure 60:
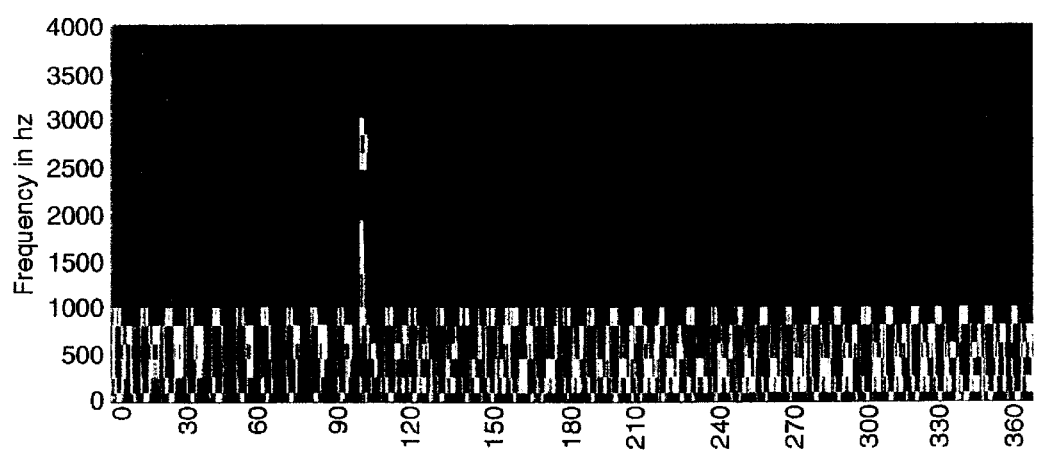
Figure 62:
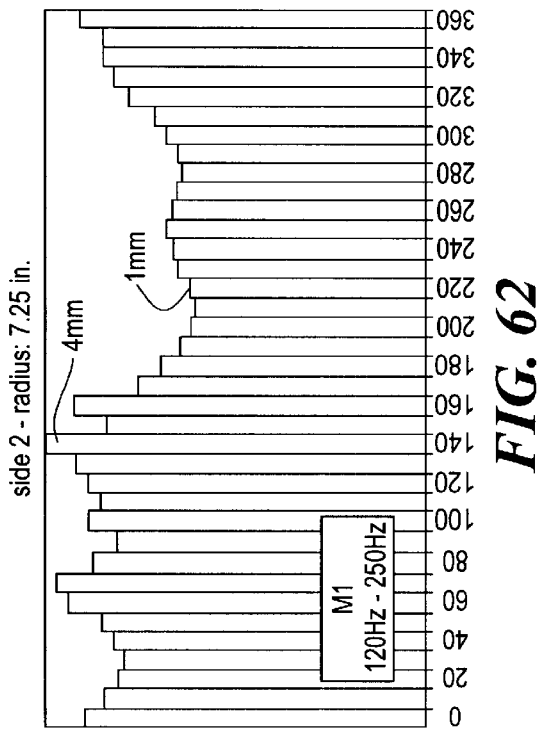
Figure 61:
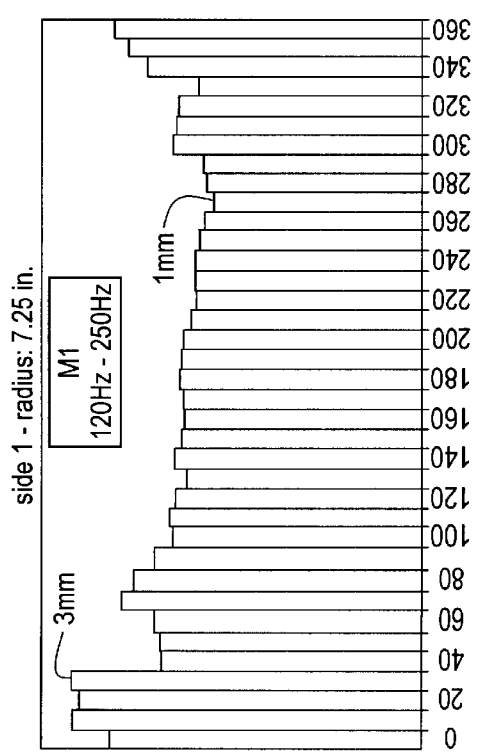
Figure 63:
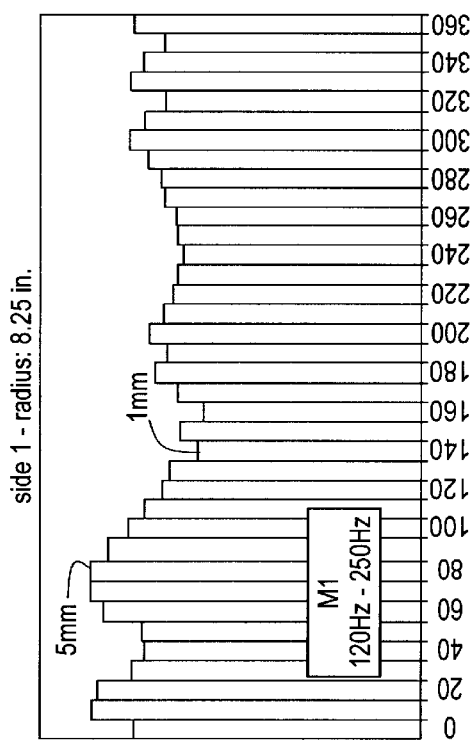

In order to train a neural network to recognize defects, data is recorded for three separate radii on each side of a tire with known delaminations and for three height positions on the threadwall of the tire. Each track included thirty-six impact points separated by a 10° rotation of the tire. For every impact on the tire, the discriminator quantities explained above are calculated by the computer. FIGS. 16–36 show the discriminator quantities for each impact at a radius of 7.25 inches on one side of the tire. FIGS. 37–57 show the discriminator quantities for each impact at a radius of 9.25 inches on the other side of the tire. FIGS. 58–60 show the general overview of the impact frequency response of one side of the tire at the radius of 7.25 inches, 8.25 inches, and 9.25 inches respectively.

An analysis was also conducted to determine the effect of the lettering present on the sidewall of a tire on the discriminator quantities described above. A typical tire sidewall contains lettering and other molded features which may interfere with the hammer impact and hence were expected to produce artifacts in the resulting discriminator quantities. This was particularly true for the middle track on each side of the tire, which ran directly through large sections of lettering. For example, at a radius of 8.25 inches, several of the quantities show an indication at 30°, particularly M3, M4, RMS, AREA, LEN 1, and PER 1. These results directly correspond to a raised impression in the molding of the surface rubber of the tire. In this type of raised feature, the tip of the impact hammer does not make fall contact with the surface of the tire and thus produces a different type of waveform than normal. This is also true in cases where the tip of the hammer hits the edge of a raised letter as is in the case at 140° and to a lesser extent at 160° and 320°. Direct full flat hits on surface lettering did not seem to affect the discriminator quantities. Thus, in the preferred embodiment, the diameter of the solenoid impact head should be decreased as much as possible to lower the chance of these glancing impacts and thus result in fewer false indicators of defects. Another surface feature that shows up in the results is the unevenness of the tire width. The distance between the solenoid and microphone fixture from the surface of the tires varies from near contact with the head of the solenoid to approximately six millimeters along the middle track. These variations are of a lesser degree along the inner track and slightly greater along the outer track. These variations in tire width effect the initial force and thus the shape of the overall impact. This is evident in lowest band in the frequency domain and FIGS. 61–66 show the high and low points marked on the various M1 discriminator quantity graphs. This variation only appears in the M1 and SD1 quantities, and therefore these discriminator quantities are indicative of surface height but not defects on the tire. In the tread area, uneven wear on the surface produce visible results in the data. As such, M1 is not used as a contribution to indicate real defects in the tire.

Therefore, some discriminator quantities are particularly useful, while others are not. From the useful discriminator quantities, a defect transfer function is constructed to combine the discriminator quantities and thus average out the non-defect information such as surface lettering as discussed above, wall thickness, and surface to microphone separation.

The defect transfer function is a classification of an equation of the form $$T = F\left[\sum_{i=1}^{K} a_i \left[F\left[\sum_{j=1}^{N} b_j DQ_i\right]\right]\right] \quad (6)$$

Where $DQ_j$ are the discriminator quantities, N is the total number of discriminator quantities used, K is the number of intermediate transformation combination equations, $a_i$ and $b_j$ are weighting coefficients, and F is a scaling function of the type $$F(X) = \frac{2}{(1 + \exp(-x))} - 1 \quad (7)$$

T is the transfer function that take as inputs the discriminator quantities and outputs a value between 0 and 1. T is essentially the probability that a defect is located at a given point during the inspection process. The coefficients of the defect transfer functions are preferably found through an adaptive learning technique such as a neural network or with genetic algorithms. In general, the data of the different discriminator quantities for a known defect is taught to a neural network which assigns a weight to each of them in a manner that the known defect is assigned a probability of 1.

Figure 67:
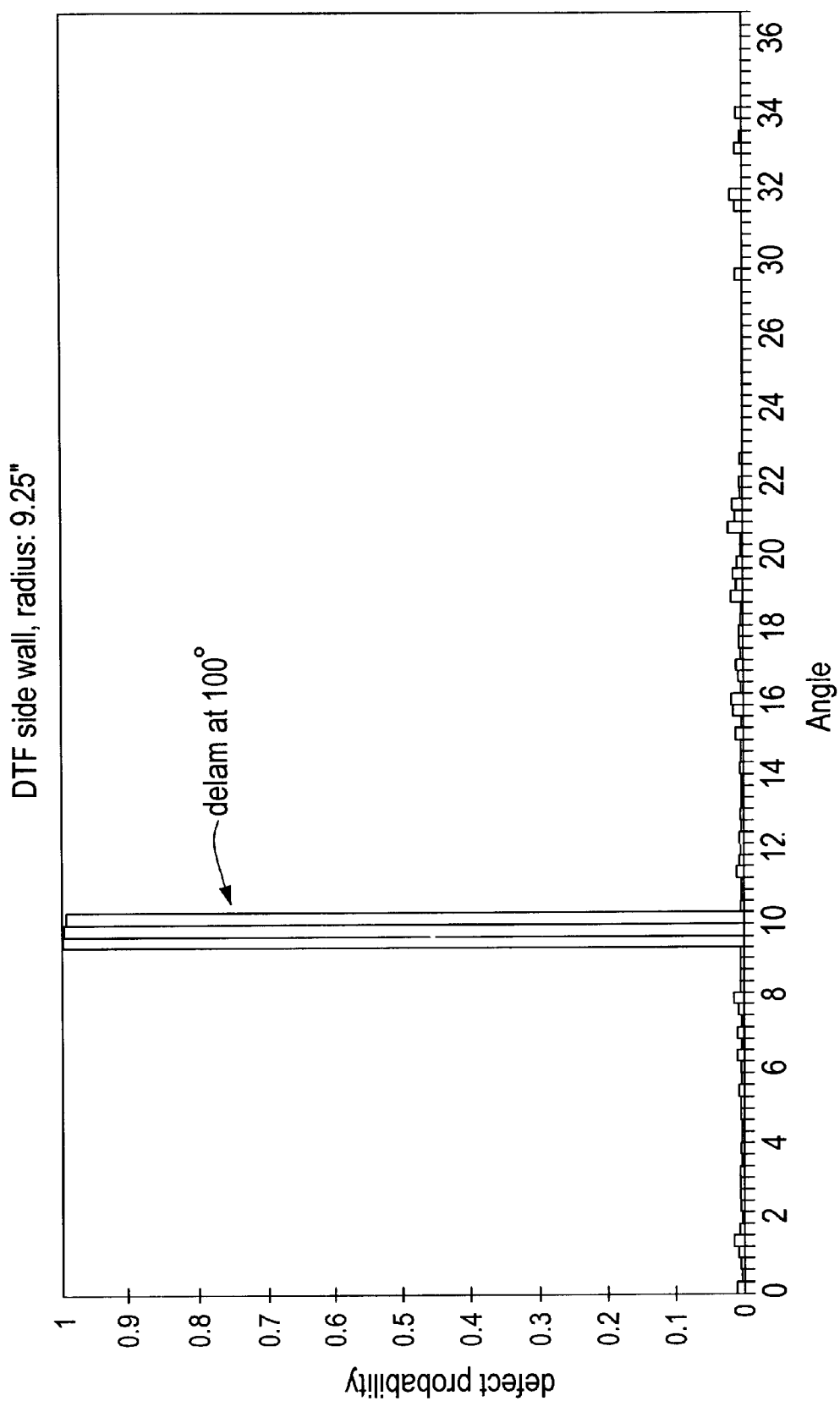
FIGS. 67 is a graph showing the defect transfer function constructed in accordance with the subject invention for a known delamination.
Figure 68:
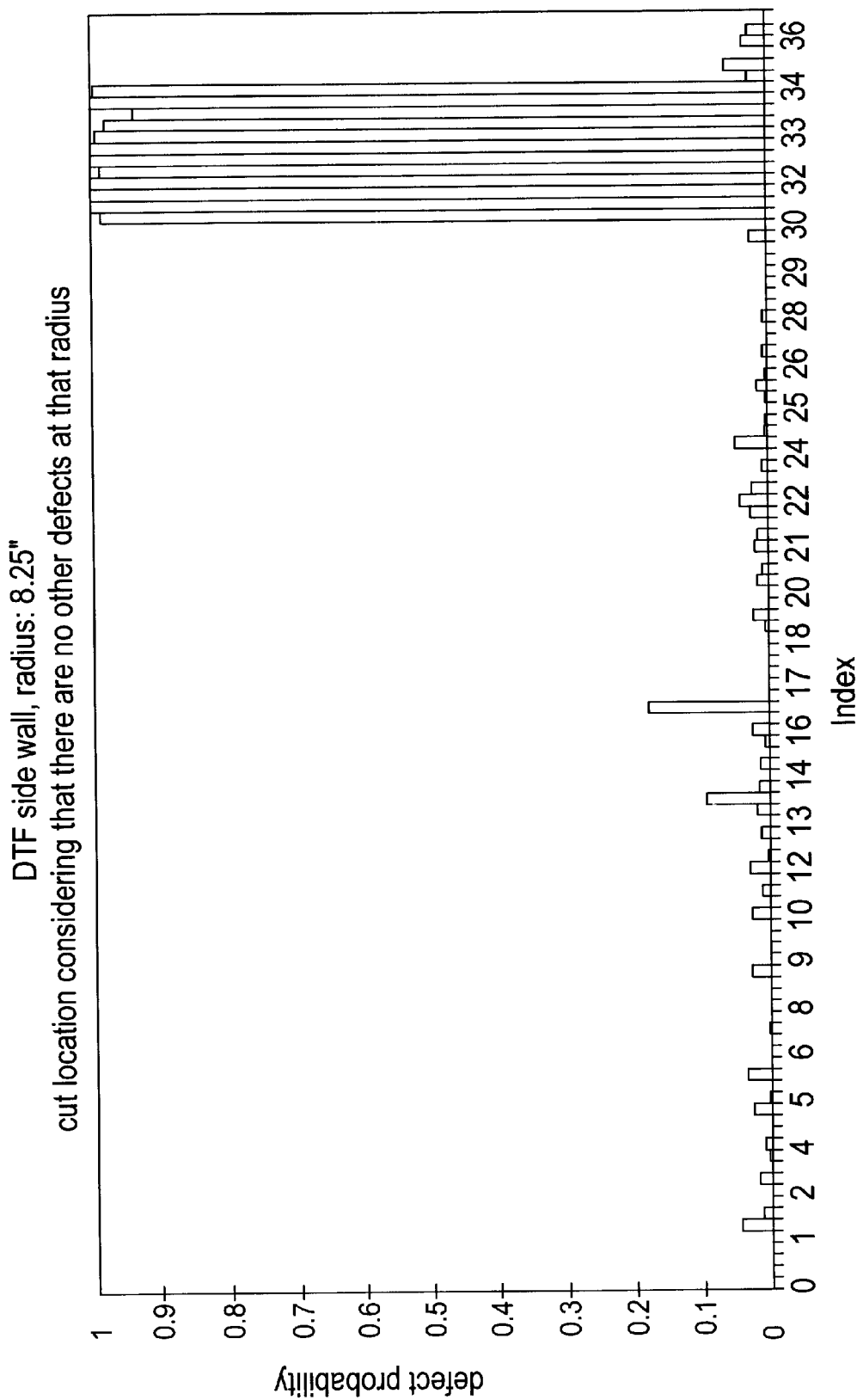
FIG. 68 is a graph showing the defect transfer function constructed in accordance with the subject invention for a tire with a known cut.

In practice, the coefficients for the data transfer function were found by training a three-level back propagation neural network using "Neuro Shell 2", an artificial neural network computer program from Ward Systems Group on roughly half of the data samples chosen at random. The data transfer functions were created for a track with a known delamination as shown in FIG. 67 and a track with a known cut in the tire as shown in FIG. 68.

Figure 69:
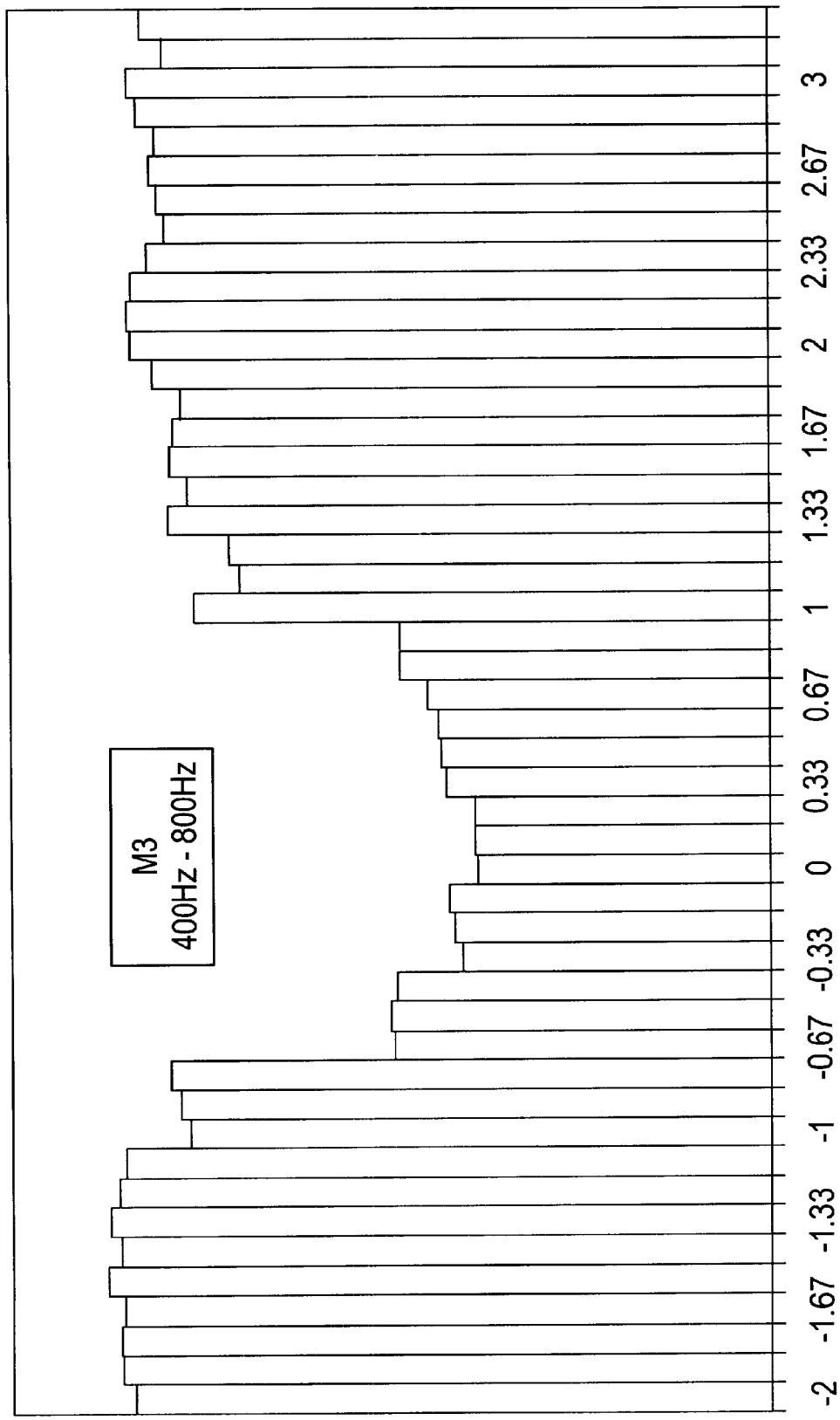
FIGS. 69–70 are graphs of two different discriminator quantities calculated in accordance with the subject invention showing the results of the spatial resolution study conducted in accordance with the subject invention.
Figure 70:
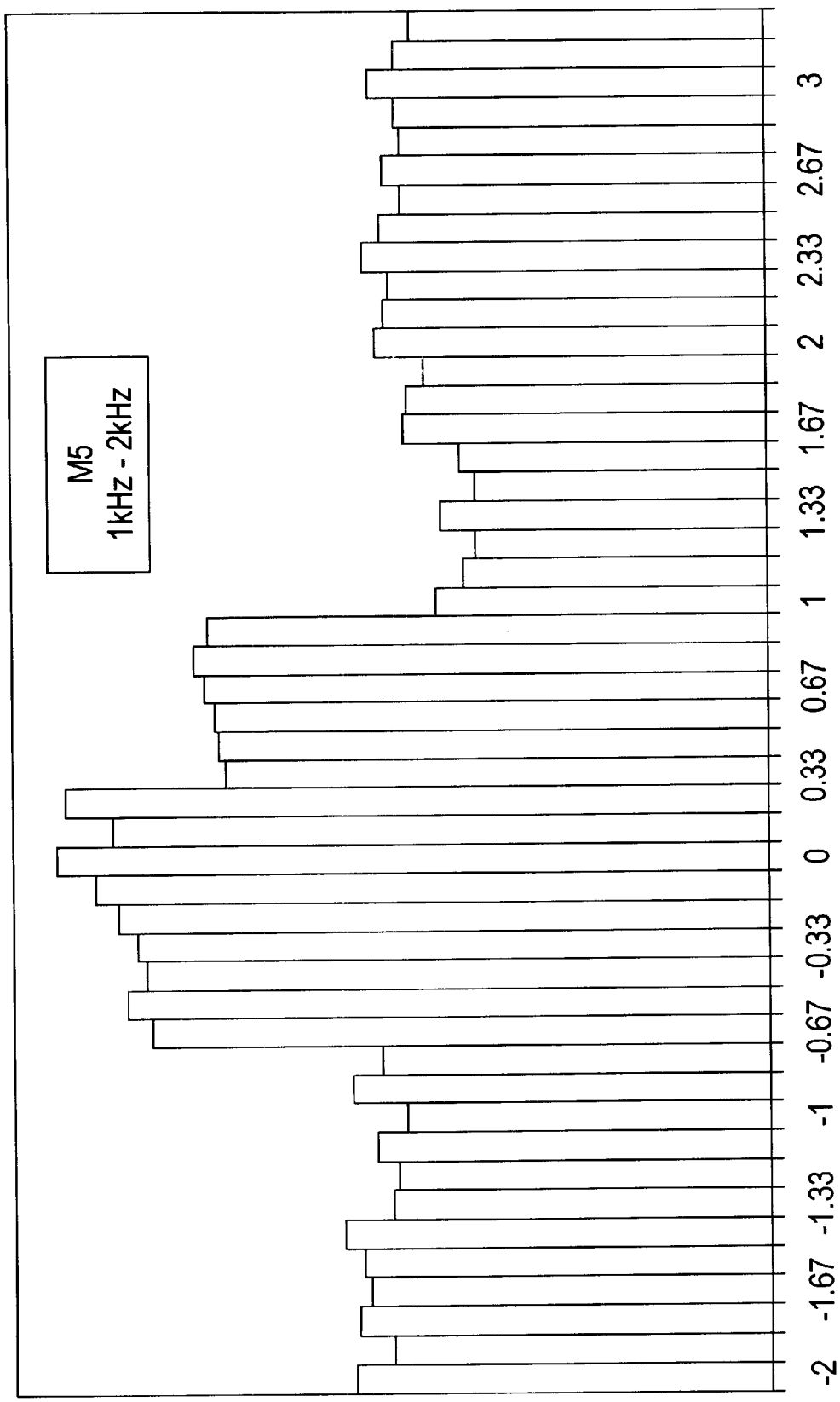

A study was also performed to determine the spatial resolution to detect a delamination. A tire with a known delamination cut into the side wall was tested by recording impact data while moving the solenoid/microphone fixture to the left and right of the defect in 0.3 inch steps and tapping three times in each position. The delamination was known to be approximately one inch wide. Results are shown in FIGS. 69 and 70. The distance in inches shown along the bottom of each graph is the relative position of the impact hammer with respect to the center of the delamination. The results indicate a defect up to 0.6 of an inch away from the center but not at 1 inch. These results suggest that the microphone location is not critical because the defect indicators are not due to the modulation of a transverse wave traveling through the defect, but instead the indicators are due to the modulation of the impact itself because of an alteration in the local material bulk properties due to the nearby existence of the defect. Thus, the positioning of the microphone is not critical and in fact one microphone might be used to record impacts from several solenoids in an array along the radius of a tire. The results also suggest that the hammer does not necessarily have to strike the tire directly over the defect. That there is no indication at 1 inch shows that there was no measurable disturbance of the impact at that distance. However, a stronger impact may cause a measurable modulation of the impact which would then produce an indicator in the discriminator quantities.

Figure 71:
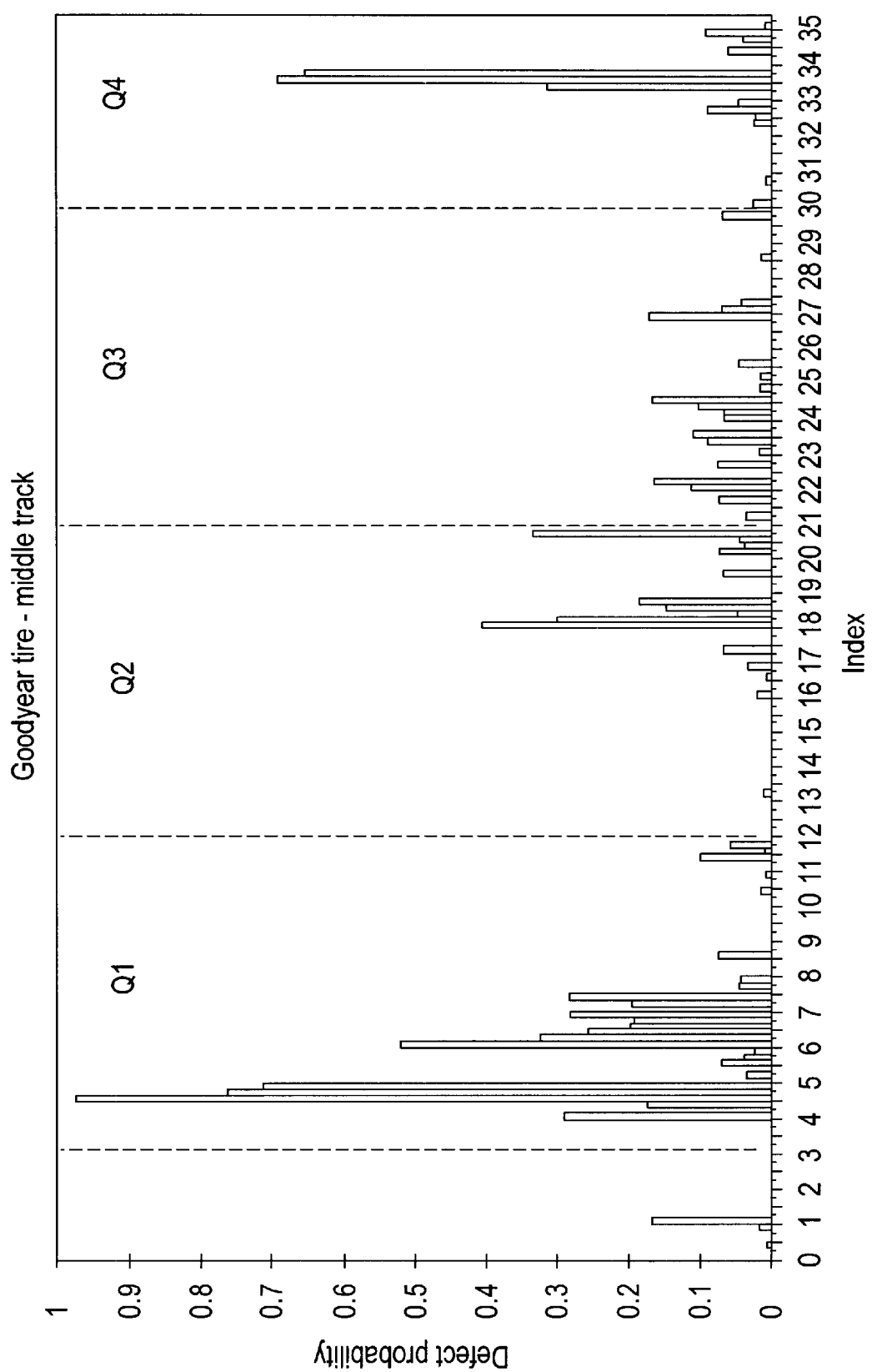
FIG. 71 is a graph showing the location of defects found by the tire defect system of the subject invention based on one track.
Figure 72:
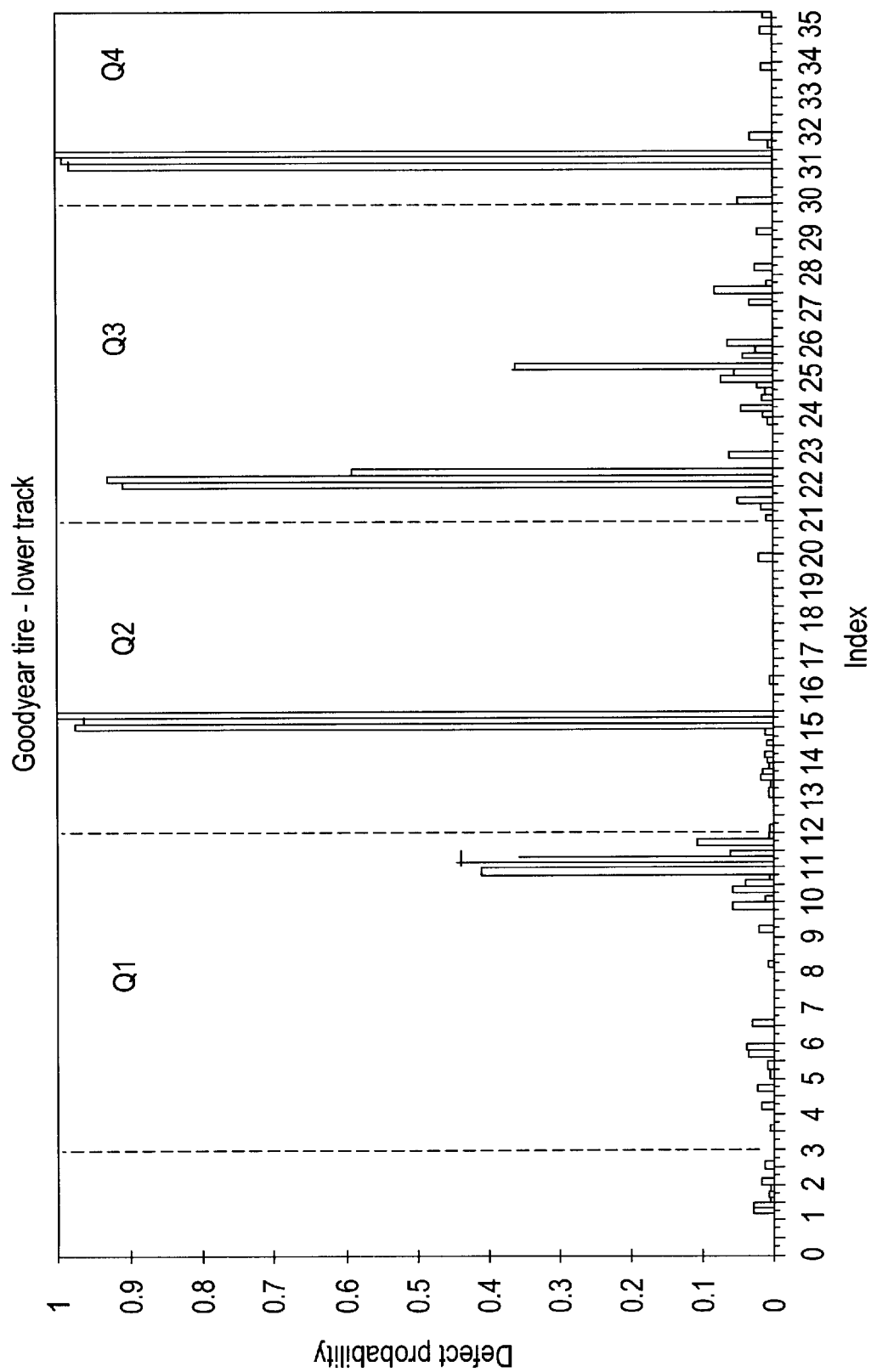
FIG. 72 is a graph showing location of defects detected in accordance with the subject invention based on another track.

Finally, the trained neural network was used to test a tire with planted defects unknown to the test engineers. The results are shown in FIGS. 71 and 72 for two tracks. The results were then compared to a map of the planted defects and the correlation was almost perfect. Note that since three samples were taken at each test point, there are three bars for each location. The test points were approximately 1 inch apart and the index points are approximately 2 inches apart. Thirty five index points marked on the tire correspond to 70 test points. Thus, the test points fall on each index mark and also halfway between. Note that the large spikes (index locations 15, 22, and 31 in FIG. 72) correlate very well to the map locations of the two larger sides delaminations. There is also a very good correspondence between the locations indicated in the middle track FIG. 71 relative to the larger side delamination show larger delaminations. The smaller delaminations under ½ inch do not show up very well in this measurement but such delaminations are below the size specified in military specification MIL-R-7726H.

Figure 73:
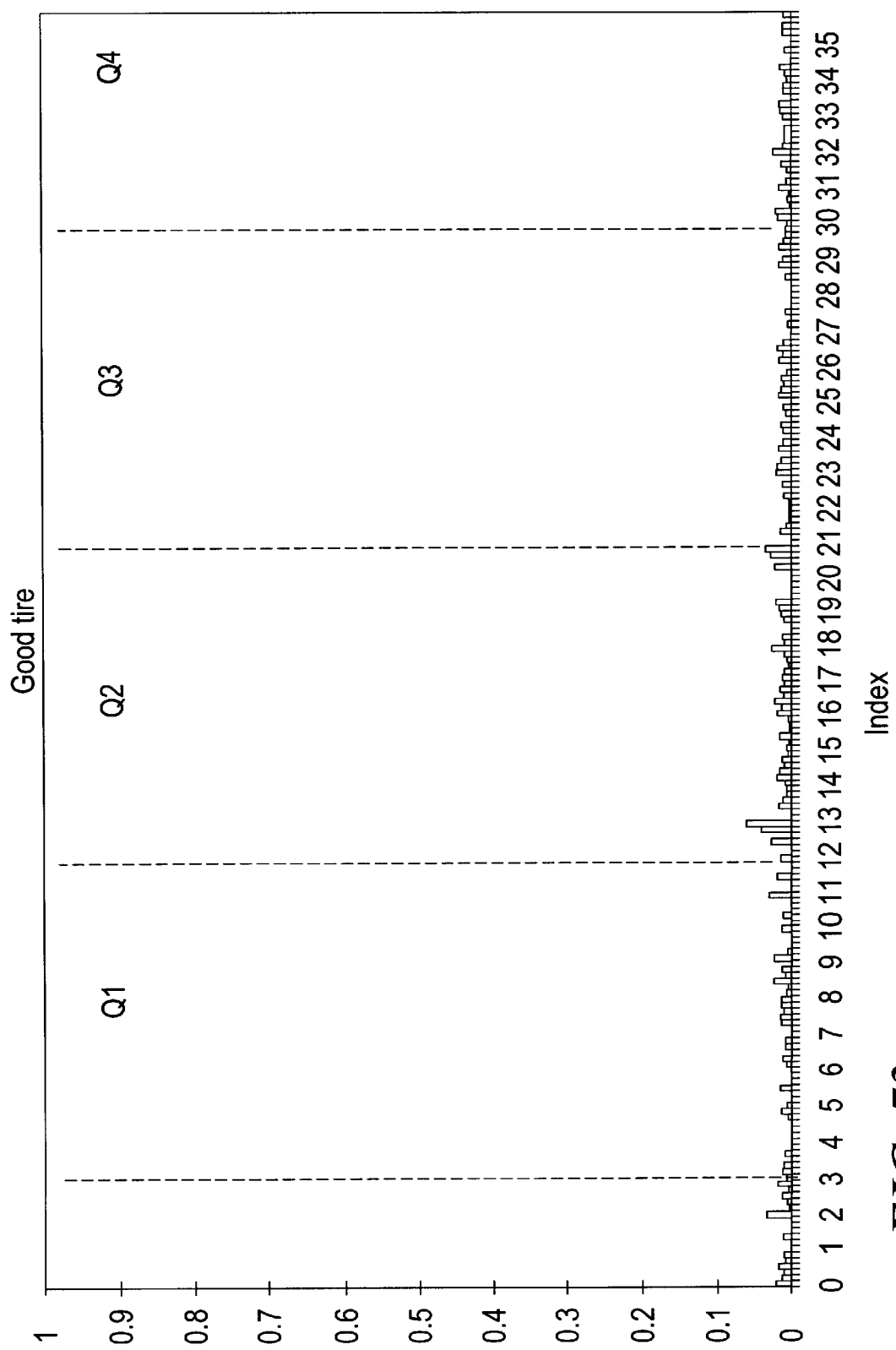
FIG. 73 is a graph of the defect transfer function constructed in accordance with the subject invention with respect to a tire without any defects.
Figure 74:
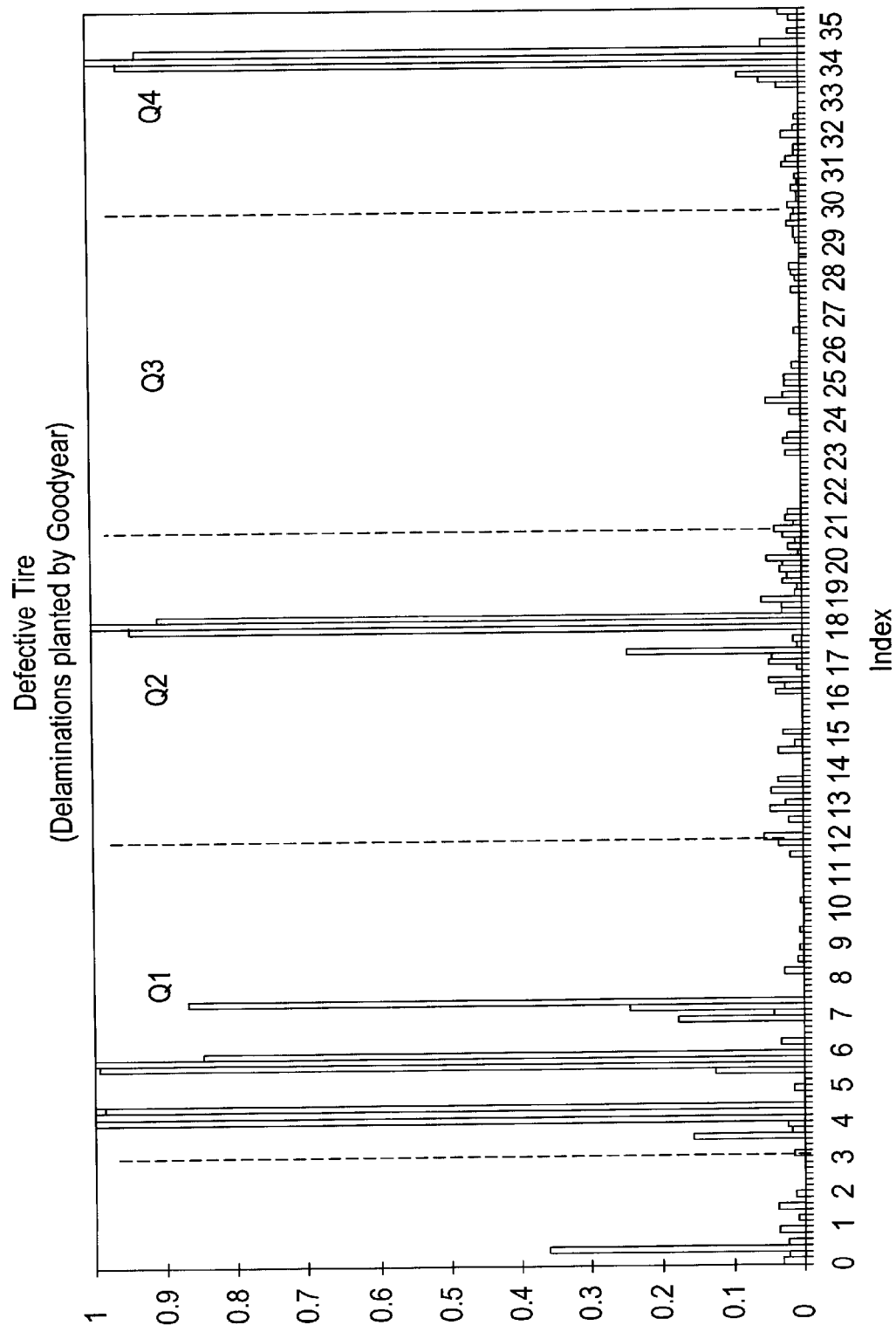
FIG. 74 is a graph of the defect transfer function constructed in accordance with the subject invention after the neural network was trained using a tire with known defects to then detect defects in a tire with unknown defects.

In any case, to detect even delaminations of this size, a stronger solenoid/hammer can be used (namely the SP100 model described above) and the tire reaction signals were processed as described above with a new defect transfer function found using data from a tire with no defects, and a tire with planted defects. Results are shown in FIG. 73 (good tire) and 74 (tire with planted delaminations).

Figure 75:
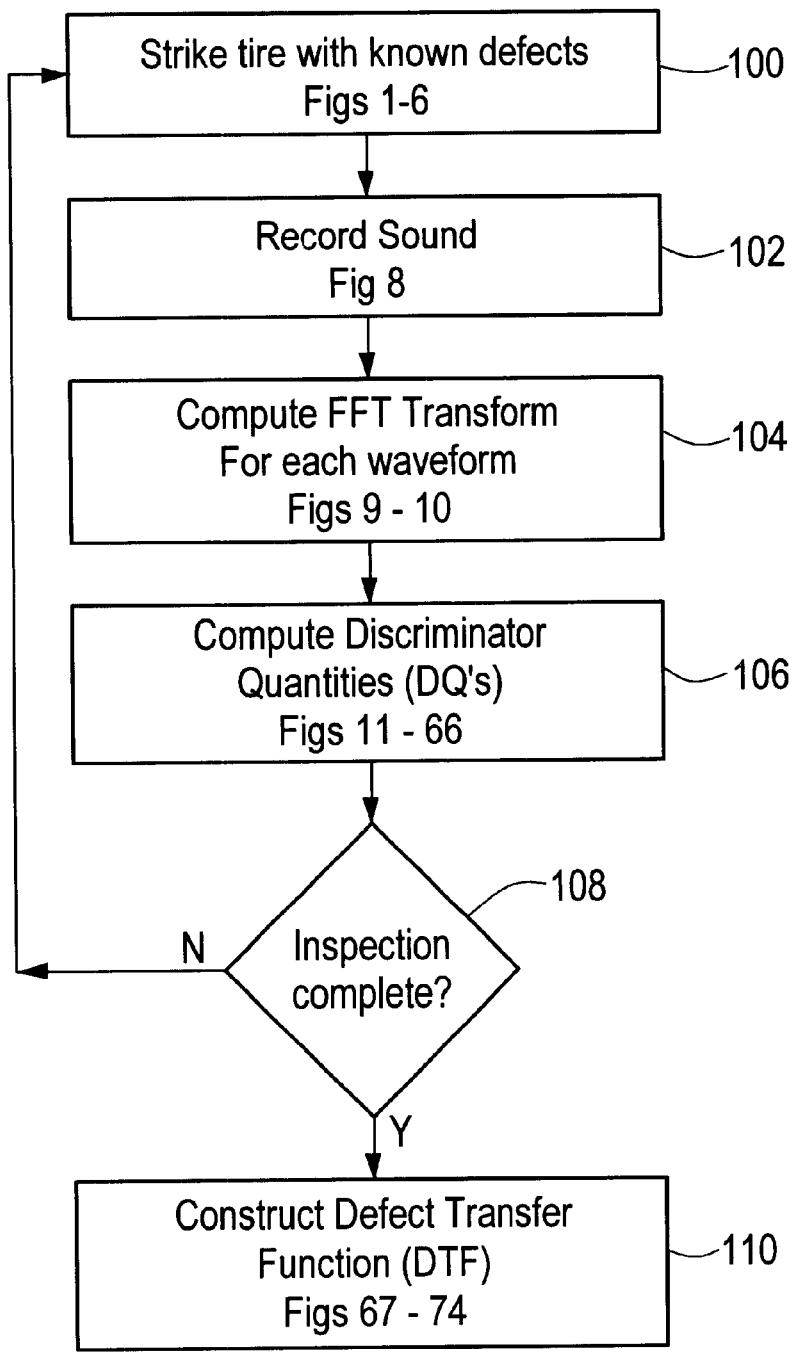
FIG. 75 is a flow chart depicting the primary steps associated with training the neural network in accordance with the tire defect detection method of the subject invention.

In summary then, in accordance with this invention, a neural network is trained to recognize delaminations, cuts, and similar defects in a tire by first striking a tire with known defects, step 100, FIG. 75 using system 10, FIGS. 1–6. The resulting sound wave is recorded, step 102, and an FFT transform is computed for each wave form, step 104. The discriminator quantities described above, are then computed, step 106 based on the FFT transform and the sound waves until the inspection is complete, step 108. The discriminator quantities calculated in step 106, are then used to construct the defect transfer function referred to above, step 110. The actual tire under inspection, is then placed on support structure 12, FIG. 1 and this tire is inspected by striking the tire with the solenoid, step 120, FIG. 76, recording the resulting sound wave, step 122, computing the FFT transform for each recorded wave form, step 124, and computing the discriminator quantities, step 126. Once the inspection is complete, step 128, the defect transfer function is constructed, step 130 and the defects displayed, step 132.

As indicated above, this process can be automated in a fashion similar to machines currently used to balance tires by providing three separate arrays of solenoid/microphone sub-assemblies 200, 202, 204, FIG. 77 each disposed about the tire on opposite sides thereof and along the threadwall for impacting the tire along three separate tracks as motor 206 rotates the tire under the control of controller 208 which also automatically activates the solenoid at the appropriate times and which includes a computer responsive to the microphone to perform the analysis described above in real time. Display 24 then provides a record of the defects as shown in FIG. 7. Such a system is expected to cost less than $20,000.00. A hand held unit which can be used to inspect tires in situ is expected to cost less than $10,000,00 and in both embodiments the inspection times are expected to be less than ten minutes.

Therefore the tire defect detection system and method of this invention accurately detects defects in a tire at a low cost and involves minimum inspection times. The tire defect detection system and method of this invention is also capable of inspecting 100% of the tire thereby increasing the reliability of the test. Operator subjectivity is eliminated and the test can be easily automated. The tire defect detection system described herein incorporates many commercial off-the-shelf components to further reduce the system price.

The code which is used to compute the FFT transform, FIGS. 75–76, to compute the discriminator quantities, and to construct the defect transfer function in accordance with the subject invention is as follows.

```
tire_inspector.ccp -- calculates discriminator values over a number of
     fixed record lengths.
  writen by Frank Heirtzler
               SEPT 1997
********************************************************************/
#include <stdlib.h>
#include <stdio.h>
#include <math.h>
#include <conio.h>
#include <string.h>
#define NPOINTS   1024
#define MINF0     0
#define MAXF0     120
#define MINF1     120
#define MAXF1     250
#define MINF2     250
#define MAXF2     400
#define MINF3     400
#define MAXF3     800
#define MINF4     800
#define MAXF4     1000
#define MINF5     1000
#define MAXF5     2000
#define MINF6     2000
#define MAXF6     3000
#define MINF7     3000
#define MAXF7     4000
#define NBAND     8
#define RATE      48000
#define THRESH    5000
#define HOPOVER   3 * 1024
#define SCALE     65536.0
struct cmplx
   {
   float re;
   float im;
   } dat [NPOINTS];   // working array for the FFT
enum logic {NO, YES};
enum level (LOW, MID, HIGH};
enum stat {OFF, ON};
float d[NPOINTS];       // input data array
float hCross;           // 1 stdev above mean
float lCross;           // 1 stdev below mean
```

-continued

```
main( )
{
    float   disp;              // waveform input
    float   scalefactor;       // frequency conversion factor
    float   dsum;              // sum for computing mean
    float   dmeaBAND];         // mean value of fft intensity
    float   dsd[BAND];         // atandard deviation
    float   dmax,              // max intensity between MINF and MAXF
    float   dmin;              // min intensity between MINF and MAXF
    float   dcurrent,          // current fft value
    float   drange[NBAND];     // dist between min and max values
    int     i;                 // loop counter
    int     band;              // frequency band counter
    int     j;                 // loop counter
    int     k;                 // loop counter
    int     count;             // theshold cross counter
    int     imin[NBAND];       // array index for MINF
    int     imax[NBAND];       // array index for MAXF
    int     ndetect;           // # data points above THRESH
    int     npoints;           // # of points read from the sample
    int     powerOf2;          // binary power of input array
    int     wv;                // wave counter
    void    fft(int m);        // fft routine
    enum level curFlag;        //staus of current point
    float   dimag;             // square of imaginary comp
    float   dreal;             // square of real comp
    float   dxlength1;         //current length
    float   dxlength2;         //current length above hCross
    enum level flagStat( );    //function returns current status
    float   metrics[11 + 2 * NBAND];    //output metrics in an array
    int     nhCross;           //# pos. peaks
    int     nhlCross;          //# pos. to neg. periods
    int     nperiod1;          //# wavelengths
    enum level oldFlag;        //status of previous x
    enum stat periodFlag;      //flags start of pos peak
    int     perstart;          //start of wavelength
    int     pulsewidth;        //width of pos. peaks
    float   slope;             //inverse slope of autocorrelation function
    enum stat startFlag;       //flags beginning of pos to neg crossing
    int     startime;          //beginning of pos. peak
    int     startpeak;         //beginning of a pos. to neg crossing
    float   xareal;            //area above hCross
    float   xcorr;             //autocorrelation function
    float   xlength1;          //length of waveform
    float   xlength2;          //length of pos peaks
    float   xperiod1;          //period between pos peaks
    float   xperiod2;          //period between pos and neg peaks
    float   xmean;             //average x
    float   xrms;              //RMS value of x
    float   xsmean;            //average x*x
    float   xssum;             //summation holder for x*x
    float   xstdev;            //standard deviation of x
    float   xsum;              //summation holder for x
    for(wv=0; wv<3; wv++)      // process three waves
    {
    // look for the impact - read in the waveform po until three
    // succesive points fall above the impact threshold
    ndetect = 0;
    do                         // read in data points
        {
        disp = GetDataPoint( );
        if (disp < 0.09) disp *= -1;
        if (disp > THRESH) ndetect++;
        } while ((ndetect < 3) && !timeOut( ));
    if (ndetect == 0) ImpactOK = NO;
    // impact has been detected, start saving the data
    if (ImpactOK)
        {
        npoints = 0;
        do                     // collect and scale NPOINTS of data points
            {
            disp = GetDataPoint( );
            disp = 10.0 * (disp/SCALE);
            d[npoints] = disp;
            npoints++;
            } while ({npoints < NPOINTS) && !timeOut( )};
        powerOf2 = (int) (log(npoints)/log(2));  //order of FFT
        xsum = d[0];           // initialize collection sums
        xssum = d[0] * d[0];
```

```
            xcorr = 0;
            xlength1 = 0;
            // first group calculations
            for (i=1; i<npoints; i++)
                {
                xsum += d[i]
                xssum += d[i] * d[i];
                xcorr += d[i] * d[i-1];
                xlength1 += d[i] - d[i-1];
                if (xlength1 < 0) xlength1 = -xlength1;
                }
            if (npoints > 1)
                {
                xmean = xsum/npoints;        //mean
                xsmean = xssum/npoints;      //mean square
                xrms = metrics[0] = sqrt[xsmean]; //root mean square
                xcorr /= npoints;
                num = (float)npoints;
                xev = metrics[1] = sqrt((num * xssum -
                xsum * xsum)/(num * (num - 1)));     //stdev
                slope = metrics[2] = (xsmean - xmean * xmean)/(xsmean - xcorr);   //autocorr
elation
                }
            /* second group calculations */
            hCross = xmean + xstdev;
            lCross = xmean - xstdev;
            startFlag = OFF;
            periodFlag = OFF;
            xareal = 0;           //area above hCross
            nhCross = 0           //# high crossings
            nhlCross = 0          //# high to low crossings
            xlength1 = 0;         //total length of waveform
            xlength2 = 0;         //length above hCross
            xperiod1 = 0;         //period between pos peaks
            xperiod2 = 0;              //period between pos and neg peaks
            pulsewidth = 0;            //width of positive peaks
            nperiod1 = 0;
            startime = 0;
            startpeak = 0;
            if (d[0] = hCross) oldFlag = HIGH;
            else if (d[0] < 1Cross) oldFlag = LOW;
            else oldFlag = MID;
            for (i=1; i<npoints; i++)
                {
                dxlength1 = d[i] - d[i-1]; //total length
                if (dxlength1 < 0) dxlength1 = -dxlength1;
                xlength1 += dxlength1;
                curFlag = flagStat(d[i]);
                if (curFlag == HIGH)
                    {
                    xareal += d[i] - hCross;    //area above hCross
                    if (oldFlag != HIGH)
                        {
                        dxlength2 = d[i] - hCross;
                        if (dxlength2 < 0) dxlength2 = -dxlength2;
                        xlength2 += dxlength2;
                        nhCross++;    //# hCross crossings
                        startime = i;       //beginning of peak
                        if (startFlag == OFF)
                            {
                            startFlag = ON;
                            startpeak = i;
                            }
                        else
                            {
                            startFlag = OFF;
                            xperiod1 += i - startpeak;
                            nperiod1++;
                            if (periodFlag == OFF)
                                {
                                periodFlag = ON;
                                perstart = i;
                                }
                            }
                        } //end if oldFlag
                    else
                        {
                        dxlength2 = d[i] - d[i-1];
                        if (dxlength2 < 0) dxlength2 = -dxlength2;
                        xlength2 += dxlength2;
```

-continued

```
                        }
                    } //end if curFlag
                else    //if curFlag != HIGH
                    {
                    if (oldFlag == HIGH) pulsewidth += (i - startime);
                    if ((curFlag == LOW) && (oldFlag != LOW) && (periodFlag == ON))
                        {
                        periodFlag = OFF;           //beginning of pos peak
                        xperiod2 += i - perstart;
                        nhlCross++;
                        }
                    oldFlag = curFlag;
                    }
            //end for i
            if (nperiod1 > 0) xperiod1 /= (float)nperiod1;
            if (nhlCross > 0) xperiod2 /= (float)nhlCross;
            metrics[3] = xareal;
            metrics[4] = nhCross;
            metrics[5] = nhlCross;
            metrics[6] = xlength1;
            metrics[7] = xlength2;
            metrics[8] = xperiod1;
            metrics[9] = xperiod2;
            metrics[10] = pulsewidth;
            for (i=0; i<NPOINTS; i++)
                {
                dat[i].re = d[i];       // real part
                dat[i].im = 0;          // imag part
                }
            fft(powerOf2);      // perform an FFT
                for i<npoints/2; i++)    // recombine al and imag
                    dreal = dat[i].re + dat[i].re;
                    dimag = dat[i].im + dat[i].im;
                    d[i] = sqrt(dreal + dimag);
                    }
            scalefactor = pow(2,powerOf2) / (float)RATE;   // frequency conversion factor
            ScaleRange(imin.imax; // calculates index for frequency limits
                                        // in each range
            // compute the output info
            for (band=0; band<NBAND; band++)
                {
                dsum = 0;
                for (i=imin(band); i<imax[band]; i++)
                    {
                    dcurrent = d[j];        // current fft value
                    dsum += dcurrent;
                    }
                dmean[band] = metrics[11+[2 * band)] = dsum/(imax[band] - imin[band]);    //
MEAN intensity
                dsum = 0;       // standard deviation
                for (i=imin[band]; i<imax[band]; i++)
                    {
                            dsum += pow((d[i] - dmean(band)), 2);
                            }
                        dsd[band] = metrics(12+(2 * band)] = sqrt(dsum/NPOINTS);
                        } //end for band
                    // output the info
                    DataPrint(metrics); //prints output metrics
                } // end for wv
            } // end for j
    return (0)
} // end main
/*************************************************************
flagStat -- returns the staus on the current value of the
        input function and whether it's below, within or
        above 1 standard deviation from the mean: LOW, MID,
        HIGH
*************************************************************/
enum level flagStat(double x)
{
    if (x > hCross) return HIGH;
    else if (x > lCross) return LOW;
    else return MID;
}
/*************************************************************
fft - In-place radix 2 decimation in time FFT
Requires pointer to complex array, x and power of 2 size of FFT, m
```

```
(size of FFT = 2**m). Places FFT output on top of input COMPLEX array.
void fft(complx *x, int m)
******************************************************************/
void fft(int m)
{
    static struct complx *w;      /* used to store the w complex array */
    static int mstore = 0;        /* stores m for future reference */
    static int n = 1;             /* length of fft stored for future */
    struct complx u,temp,tm;
    struct complx *xi,*xip,*xj,*wptr;
    int i,j,k,l,le,windex;
    double arg, w_real, w_imag, wrecur_real, wrecur_imag, wtemp_real;
    if(m != mstore) {
/* free previously allocated storage and set new m
        if(mstore != 0) free(w);
        mstore = m;
        if(m == 0) return;        /* if m =0 then done */
/* n = 2**m = fft length */
        n = 1 << m;
        le = n/2;
/* allocate the storage for w */
        w = (struct complx *) calloc(le-1,sizeof(struct complx));
        if(!w) {
            printf(*\nUnable to allocate complex W array\n*);
            exit(1);
        }
/* calculate the w values recursively */
        arg = 4.0*atan(1.0)/le;   /* PI/le calculation */
        wrecur_= w_real = cos(arg);
        wrecur_imag = w_imag = -sin(arg);
        xj = w;
        for (j = 1; j < le ; j++) {
            xj->re = (float)wrecur_real;
            xj->im = (float)wrecur_imag;
            xj++;
            wtemp_real = wrecur_real * w_real - wrecur_imag * w_imag;
            wrecur_imag = wrecur_real * w_imag + wrecur_imag * w_real;
            wrecur_real = wtemp_real;
        }
    }
/* start fft */
    le = n;
    windex = 1;
    for (l = 0; l < m; l++) {
        le = le/2;
/* first iteration with no multiplies */
        for(i = 0; i < n ; i = i + 2*le) {
            xi = dat + i;
            xip = xi + le;
            temp.re = xi->re + xip->re;
            temp.im = xi->im - xip->im;
            tm.re = ci->re xip->re;
            tm.re = xi->im - xip->im;
            xip->re = tm.re * u.re - tm.im + u.im;
            xip->im = tm.re * u.im + tm.im + u.re;
            *xi - temp;
        }
        wptr = wptr + windex;
    }
    windex = 2*windex;
}
/* rearrange data by bit reversing */
    j = 0;
    for (i = 1 ; i < (n-1) ; i++) {
        k = n/2;
        while(k >= j) {
            j = j - k;
            k = k/2;
        }
        j = j + k;
        if (i < j) {
            xi = dat + i;
            xj = dat + j;
            temp = *xj;
            *xj = *xi;
            *xi = temp;
        }
    }
}
```

-continued

```
/**************************************************************
    /*** absolute( ) -- returns the absosulte value of its double
                        argment.    ***/
double absolute(double arg)
{
    if (arg >= 0) return arg;
    else return -arg;
}
**************************************************************/
```

Although specific features of this invention are shown in some drawings and not others, this is for convenience only as each feature may be combined with any or all of the other features in accordance with the invention. Other embodiments will occur to those skilled in the art and are within the following claims. For example, although the disclosure above relates in particular to inspecting tires after they have been retreaded, the system and method of this invention can be used to inspect tires before they are retreaded for retreading feasibility and/or to inspect tires generally after manufacture or during use.

What is claimed is:

1. A tire defect detection system comprising:
   a support structure for receiving a tire;
   an actuator disposed proximate the tire for impacting the tire;
   a microphone disposed proximate the actuator for receiving a sound wave generated when the actuator impacts the tire; and
   a computer responsive to the microphone; the computer including:
   means for calculating a plurality of discriminator quantities from the sound wave, and
   means for comparing the calculated discriminator quantities with stored discriminator quantities indicative of a defect to determine whether a defect is present in the tire.

2. The tire defect detection system of claim 1 in which the actuator includes an impactor.

3. The tire defect detection system of claim 1 further including a controller for driving the actuator at an impact time of less than 0.1 seconds.

4. The tire defect detection system of claim 1 in which the microphone has a response of approximately 70–15,000 Hz.

5. The tire defect detection system of claim 1 in which the means for calculating includes a routine for performing an FFT transform for each waveform.

6. The tire defect detection system of claim 5 in which the means for calculating includes means for determining the mean value of the amplitude of the FFT transform in each frequency band as discriminator quantities.

7. The tire defect detection system of claim 5 in which the means for calculating includes means for determining the standard deviation of the amplitude of the FFT transform in each frequency band as a discriminator quantity.

8. The tire defect detection system of claim 7 in which the means for calculating includes means for determining the average area under each excursion above one standard deviation above the mean of the FFT transform as a discriminator quantity.

9. The tire defect detection system of claim 7 in which the means for calculating includes means for determining the average time between crossings of one standard deviation above the mean as a discriminator quantity.

10. The tire defect detection system of claim 7 in which the means for calculating includes means for determining the average time between crossings one standard deviation above the mean and one standard deviation below the mean as a discriminator quantity.

11. The tire defect detection system of claim 7 in which the means for calculating includes means for determining the average length of the FFT transform waveform above one standard deviation above the mean as a discriminator quantity.

12. The tire defect detection system of claim 7 in which the means for calculating includes means for determining the width of any pulse of the FFT transform waveform which are above one standard deviation above the mean as a discriminator quantity.

13. The tire defect detection system of claim 5 in which the means for calculating includes means for determining the root mean square of the FFT transform as a discriminator quantity.

14. The tire defect detection system of claim 5 in which the means for calculating includes means for determining the inverse of the autocorrelation time of the FFT transform as a discriminator quantity.

15. The tire defect detection system of claim 5 in which the means for calculating includes means for determining the average length of the FFT transform waveform as a discriminator quantity.

16. The defect detection system of claim 1 further including means for constructing a defect transfer function based on the calculated discriminator quantities.

17. A tire defect detection system comprising:
    an actuator for impacting the tire;
    a microphone disposed proximate the actuator for receiving a sound wave generated when the actuator impacts the tire; and
    a computer responsive to the microphone, the computer programmed to:
    perform an FFT transform for the sound wave, calculate a plurality of discriminator quantities from the FFT transform, and
    construct a defect transfer function based on the calculated discriminator quantities to provide an indication of whether a defect is present in the tire.

18. A method of inspecting tires for defects, the method comprising:
    obtaining a tire with known defects;
    impacting the tire with an actuator;
    recording the resulting sound waves;
    calculating a plurality of discriminator quantities for each sound wave;
    constructing a defect transfer function based on the calculated discriminator quantities and storing the coefficients thereof;

obtaining a tire with unknown defects;

impacting the unknown tire with an actuator;

recording the resulting sound waves;

calculating a plurality of discriminator quantities for each sound wave; and using the stored coefficients of the constructed defect transfer function to determine whether a defect is present in the tire with unknown defects.

19. A tire defect detection method comprising:

disposing an actuator proximate the tire and impacting the tire;

disposing a microphone proximate the actuator for receiving a sound wave generated when the actuator impacts the tire;

calculating a plurality of discriminator quantities from the sound wave; and comparing the calculated discriminator quantities with stored discriminator quantities indicative of a defect to determine whether a defect is present in the tire.

20. The tire defect detection method of claim 19 in which the impact time is less than 0.1 seconds.

21. The tire defect detection methods of claim 19 in which calculating includes performing a FFT transform for each waveform.

22. The tire defect detection method of claim 21 further including determining the mean value of the amplitude of the FFT transform in each frequency band as discriminator quantities.

23. The tire defect detection method of claim 21 further including determining the standard deviation of the amplitude of the FFT transform in each frequency band as a discriminator quantity.

24. The tire defect detection method of claim 19 further including determining the root mean square of the sound wave as a discriminator quantity.

25. The tire defect detection method of claim 19 further including determining the inverse of the autocorrelation time of the sound wave as a discriminator quantity.

26. The tire defect detection method of claim 19 further including determining the average area under each excursion above one standard deviation above the mean of the sound wave as a discriminator quantity.

27. The tire defect detection method of claim 19 further including determining the average time between crossings of one standard deviation above the means as a discriminator quantity.

28. The tire defect detection method of claim 19 further including determining the average time between crossings one standard deviation below the mean and one standard deviation below the mean as a discriminator quantity.

29. The tire defect detection method of claim 19 further including determining the average length of the sound wave as a discriminator quantity.

30. The tire defect detection method of claim 19 further including determining the average length of the sound wave above one standard deviation above the mean as a discriminator quantity.

31. The tire defect detection method of claim 19 further including determining the width of any pulse of the sound wave which is above one standard deviation above the mean as a discriminator quantity.

32. The defect detection method of claim 19 further including constructing a defect transfer function based on the calculated discriminator quantities.

33. A tire defect detection method comprising:

recording a sound wave generated when the tire is impacted;

performing a FFT transform for the sound wave;

calculating a plurality of discriminator quantities from the sound wave and FFT transform; and constructing a defect transfer function based on the calculated discriminator quantities to provide an indication of whether a defect is present in the tire.

* * * * *